US005951980A

United States Patent [19]

Collen

[11] Patent Number: 5,951,980

[45] Date of Patent: *Sep. 14, 1999

[54] IDENTIFICATION, PRODUCTION AND USE OF NEW STAPHYLOKINASE DERIVATIVES WITH REDUCED IMMUNOGENICITY

[75] Inventor: Désiré Jose Collen, Schoonzichtlaan 20, B-3020 Winksele-Herent, Belgium

[73] Assignees: Leuven Research & Development VZW; Desire Jose Collen, both of Belgium

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/784,971

[22] Filed: Jan. 16, 1997

Related U.S. Application Data

[63] Continuation-in-part of application No. 08/371,505, Jan. 11, 1995, Pat. No. 5,695,754, and application No. 08/499,092, Jul. 6, 1995.

[30] Foreign Application Priority Data

Jan. 6, 1995 [EP] European Pat. Off. .............. 95200023

[51] Int. Cl.$^6$ .......................... A61K 38/48; A61K 39/02; C12N 15/00; C12N 9/52

[52] U.S. Cl. .................................... 424/94.64; 424/190.1; 424/200.1; 435/172.1; 435/320.1; 435/220

[58] Field of Search ............................. 424/190.1, 200.1, 424/94.64; 435/172.1, 320.1, 220

[56] References Cited

U.S. PATENT DOCUMENTS

| | | | |
|---|---|---|---|
| 4,532,211 | 7/1985 | Sako et al. | 435/172.3 |
| 5,336,495 | 8/1994 | Collen et al. | 424/94.64 |
| 5,475,089 | 12/1995 | Matsuo et al. | 530/350 |

FOREIGN PATENT DOCUMENTS

| | | |
|---|---|---|
| 0721982 A1 | 7/1996 | European Pat. Off. . |
| 96/21016 A2 | 7/1996 | WIPO . |

OTHER PUBLICATIONS

Daniel et al. Mapping of linear antigenic sites on the S glycoprotein of a neurotropic murine coronavirus with synthetic peptides. Virology. vol. 202, pp. 540–549, 1994.

Gase et al. The thermostability of natural variants of bacterial plasminogen–activator staphylokinase. European Journal of Biochemistry. vol. 223, pp. 303–308, 1994.

Schlott et al. Functional properties of recombinant staphylokinase variants obtained by site–specific mutagenesis of methionine–26. Biochimica et Biophysica Acta. vol. 1204, pp. 235–242, 1994.

Collen "Coronary thrombolysis with recombinant staphylokinase in patients with evolving myocardial infarction." Circulation vol. 87: 1850–1853 (1993).

Collen et al. "Primary structure and gene structure of staphylokinase." Fibrinolysis 6: 226–231 (1992).

Collen et al. "Comparative thrombolytic and immunogenic properties of staphylokinase and streptokinase." Fibrinolysis 6: 232–242 (1992).

Collen et al. "Comparative immunogenicity and thrombolytic properties toward arterial and venous thrombi of streptokinase and recombinant staphylokinase in baboons." Circulation vol. 87: 996–1006 (1993).

*Primary Examiner*—Robert A. Wax
*Assistant Examiner*—Maryam Monshipouri
*Attorney, Agent, or Firm*—Webb Ziesenheim Logsdon Orkin & Hanson, P.C.

[57] ABSTRACT

Methods for the identification, production and use of derivatives of the invention obtained by preparing a DNA fragment comprising at least the part of the coding sequence of staphylokinase that provides for its biological activity; performing in vitro site-directed mutagenesis on the DNA fragment to replace one or more codons for wild-type amino acids by a codon for another amino acid; cloning the mutated DNA fragment in a suitable vector; transforming or transfecting a suitable host cell with the vector; and culturing the host cell under conditions suitable for expressing the DNA fragment. Preferably the DNA fragment is a 453 bp EcoRI-HindIII fragment of the plasmid pMEX602sakB, the in vitro site-directed mutagenesis is performed by spliced overlap extension polymerase chain reaction and the mutated DNA fragment is expressed in *E. coli* strain TG1 or WK6. The invention also relates to pharmaceutical compositions comprising at least one of the staphylokinase derivatives according to the invention together with a suitable excipient, for treatment of arterial thrombosis.

12 Claims, 3 Drawing Sheets

```
  1                                                                                        14
Ser Ser Ser  Phe  Asp Lys  Gly  Lys Tyr Lys  Lys Gly  Asp Asp
                   └──20─┘      └──21───┘    └────1────┘

 15                                                                                       28
Ala Ser Tyr  Phe  Glu  Pro  Thr  Gly  Pro  Tyr  Leu  Met  Val Asn
                  └22┘

 29                                                                                       42
Val Thr Gly  Val  Asp Ser Lys Gly Asn  Glu  Leu  Leu  Ser Pro
                  └──2──┘ └──3──┘

 43                                                                                       56
His Tyr Val  Glu  Phe  Ile  Lys  Pro  Gly , Thr  Thr  Leu Thr
             └─────4─────┘

 57                                                                                       70
Lys Glu Lys  Ile  Glu  Tyr  Tyr  Val  Glu  Trp  Ala  Leu  Asp Ala
└──5──┘           └─────6─────┘       └────────7────────┘

 71                                                                                       84
Thr Ala Tyr  Lys  Glu  Phe  Arg  Val  Val  Glu  Leu  Asp  Pro Ser
             └────8────┘              └─────9─────┘

 85                                                                                       98
Ala Lys Ile  Glu  Val  Thr  Tyr  Tyr  Asp Lys  Asn  Lys Lys Lys
    └──10──┘                          └──11──┘     └──12──┘

 99                                                                                      112
Glu Glu Thr  Lys  Ser  Phe  Pro  Ile  Thr  Glu Lys  Gly  Phe Val
└13┘ └──14──┘                              └──15──┘
                                              
113                                                                                      126
Val Pro Asp  Leu  Ser  Glu  His  Ile Lys  Asn  Pro  Gly  Phe Asn
        └────────16────────┘     └──17──┘

127                              136
Leu Ile Thr  Lys  Val  Val  Ile  Glu Lys Lys
             └18┘                └───19───┘
```

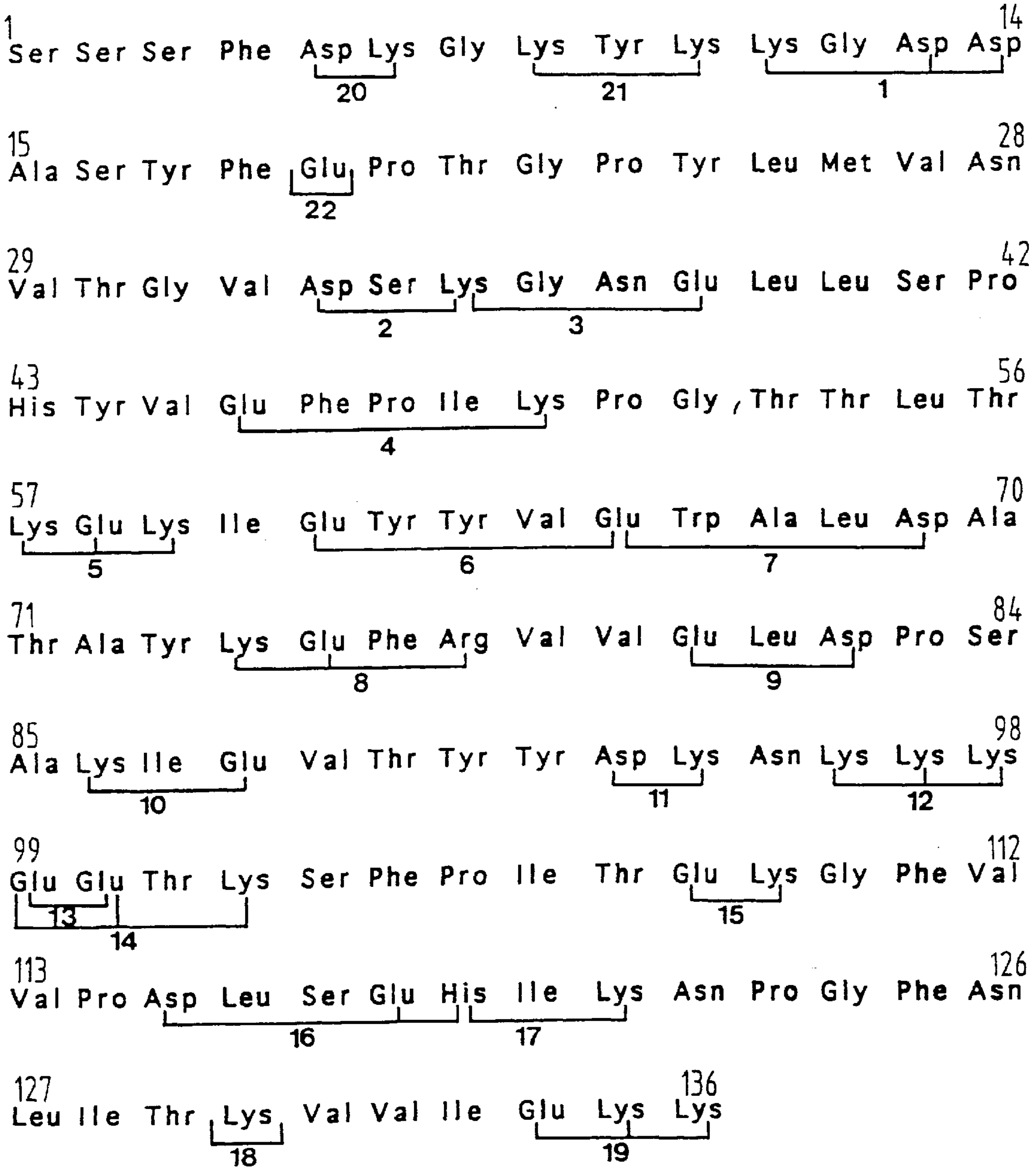

FIG. 1

IDENTIFICATION, PRODUCTION AND USE OF NEW STAPHYLOKINASE DERIVATIVES WITH REDUCED IMMUNOGENICITY

CROSS-REFERENCE TO RELATED APPLICATIONS

This is a continuation-in-part of application Ser. No. 08/371,505, filed Jan. 11, 1995, now U.S. Pat. No. 5,695,754, issued Dec. 9, 1997 and a continuation-in-part of application Ser. No. 08/449,092, filed Jul. 6, 1995.

BACKGROUND OF THE INVENTION

1. Field of the Invention

This invention relates to new staphylokinase derivatives with reduced immunogenicity, their identification, production and use in the treatment of arterial thrombosis and for the preparation of a pharmaceutical composition for treating arterial thrombosis. More in particular it relates to the use of engineered staphylokinase derivatives for the preparation of a pharmaceutical composition for treating myocardial infarction.

2. Description of the Prior Art

Staphylokinase, a protein produced by certain strains of *Staphylococcus aureus,* which was shown to have profibrinolytic properties more than 4 decades ago (1,2) appears to constitute a potent thrombolytic agent in patients with acute myocardial infarction (3,4). The staphylokinase gene has been cloned from the bacteriophages sakøC (5) and sak42D (6) as well as from the genomic DNA (sakSTAR) of a lysogenic *Staphylococcus aureus* strain (7). The staphylokinase gene encodes a protein of 163 amino acids, with amino acid 28 corresponding to the $NH_2$-terminal residue of full length mature staphylokinase (6,8,9). The mature protein sequence (SEQ ID NO:3) of the wild-type variant SakSTAR (9) is represented in FIG. 1. Only four nucleotide differences were found in the coding regions of the sakϕC, sak42D and sakSTAR genes, one of which constituted a silent mutation (6,8,9).

In a plasma milieu, staphylokinase is able to dissolve fibrin clots without associated fibrinogen degradation (10–12). This fibrin-specificity of staphylokinase is the result of reduced inhibition by $\alpha_2$-antiplasmin of plasmin.staphylokinase complex bound to fibrin, recycling of staphylokinase from the plasmin.staphylokinase complex following inhibition by $\alpha_2$-antiplasmin, and prevention of the conversion of circulating plasminogen.staphylokinase to plasmin.staphylokinase by $\alpha_2$-antiplasmin (13–15). In addition staphylokinase has a weak affinity for circulating but a high affinity for fibrin-bound plasminogen (16) and staphylokinase requires $NH_2$-terminal processing by plasmin to display its plasminogen activating potential (17). In several experimental animal models, staphylokinase appears to be equipotent to streptokinase for the dissolution of whole blood or plasma clots, but significantly more potent for the dissolution of platelet-rich or retracted thrombi (18,19).

Staphylokinase is a heterologous protein and is immunogenic in man. The intrinsic immunogenicity of staphylokinase, like that of streptokinase, clearly hampers its unrestricted use. Not only will patients with preexisting high antibody titers be refractory to the thrombolytic effect of these agents, but allergic side effects and occasional life-threatening anaphylaxis may occur (20). Because both streptokinase and staphylokinase are heterologous proteins, it is not obvious that their immunogenicity could be reduced by protein engineering. Indeed, no successful attempts to generate active low molecular weight fragments from streptokinase have been reported. In staphylokinase, deletion of the NH2-terminal 17 amino acids or the COOH-terminal 2 amino acids inactivates the molecule, which in addition is very sensitive to inactivation by site-specific mutagenesis (21).

Nevertheless, we have, surprisingly, found that the wild-type staphylokinase variant SakSTAR (9) contains three non-overlapping immunodominant epitopes, at least two of which can be eliminated by specific site-directed mutagenesis, without inactivation of the molecule (22). These engineered staphylokinase variants are less reactive with antibodies elicited in patients treated with wild-type staphylokinase, and are significantly less immunogenic than wild-type staphylokinase, as demonstrated in rabbit and baboon models and in patients with peripheral arterial occlusion (22).

SUMMARY OF THE INVENTION

The present invention relates to general methods for the identification, production and use of staphylokinase derivatives showing a reduced antigenicity and immunogenicity as compared to wild-type staphylokinase. The derivatives have essentially the amino acid sequence of wild-type staphylokinase or modified versions thereof, but have a reduced reactivity with a panel of murine monoclonal antibodies and/or with antibodies induced in patients by treatment with wild-type SakSTAR, without destroying the biological activity of the derivatives. Preferably the amino acids are replaced by alanine but several alternative possibilities are also illustrated.

The invention also relates to a method for producing the derivatives of the invention by preparing a DNA fragment comprising at least the part of the coding sequence of staphylokinase that provides for its biological activity; performing in vitro site-directed mutagenesis on the DNA fragment to replace one or more codons for wild-type amino acids by a codon for another amino acid; cloning the mutated DNA fragment in a suitable vector; transforming or transfecting a suitable host cell with the vector; and culturing the host cell under conditions suitable for expressing the DNA fragment. Preferably the DNA fragment is a 453 bp EcoRI-HindIII fragment of the plasmid pMEX602sakB (22,23), the in vitro site-directed mutagenesis is performed by spliced overlap extension polymerase chain reaction with Vent DNA polymerase (New England Biolabs) or Taq polymerase (Boehringer Mannheim) and with available or generated SakSTAR or SAKSTAR variants as template (24).

A second DNA fragment is described in connection with the present invention. The DNA fragment is a 466 bp EcoRI-HindIII fragment of the plasmid pMEX602SAK. The expression vector pMEX602SAK was kindly provided by The Institute for Molecular Biology of Jena, Germany.

The invention also relates to pharmaceutical compositions comprising at least one of the staphylokinase derivatives according to the invention together with a suitable excipient, for treatment of arterial thrombosis. Pharmaceutical compositions, containing less immunogenic staphylokinase variants as the active ingredient, for treating arterial thrombosis in human or veterinary practice may take the form of powders or solutions and may be used for intravenous, intraarterial or parental administration. Such compositions may be prepared by combining (e.g. mixing, dissolving etc.) the active compound with pharmaceutically acceptable excipients of neutral character (such as aqueous or non-aqueous solvents, stabilizers, emulsifiers, detergents, additives), and further, if necessary with dyes. The concentration of the active ingredient in a therapeutical composition may vary widely between 0.1% and 100%, dependent on the character of the disease and the mode of administration. Further the dose of the active ingredient to be administered may vary between 0.05 mg and 1.0 mg per kg of body weight.

Furthermore the invention relates to the use of the staphylokinase derivatives for the treatment of arterial thrombosis, in particular myocardial infarction, and to the use of staphylokinase derivatives for the preparation of a pharmaceutical composition for the treatment of arterial thrombosis, in particular myocardial infarction.

BRIEF DESCRIPTION OF THE DRAWINGS

FIG. 1 shows the protein sequence of wild-type staphylokinase, SakSTAR (SEQ ID NO: 5). Numbering starts with the $NH_2$-terminal amino acid of mature full length staphylokinase. The "charge-cluster to alanine" variants that were studied are indicated;

DETAILED DESCRIPTION OF THE INVENTION

Figure 2:
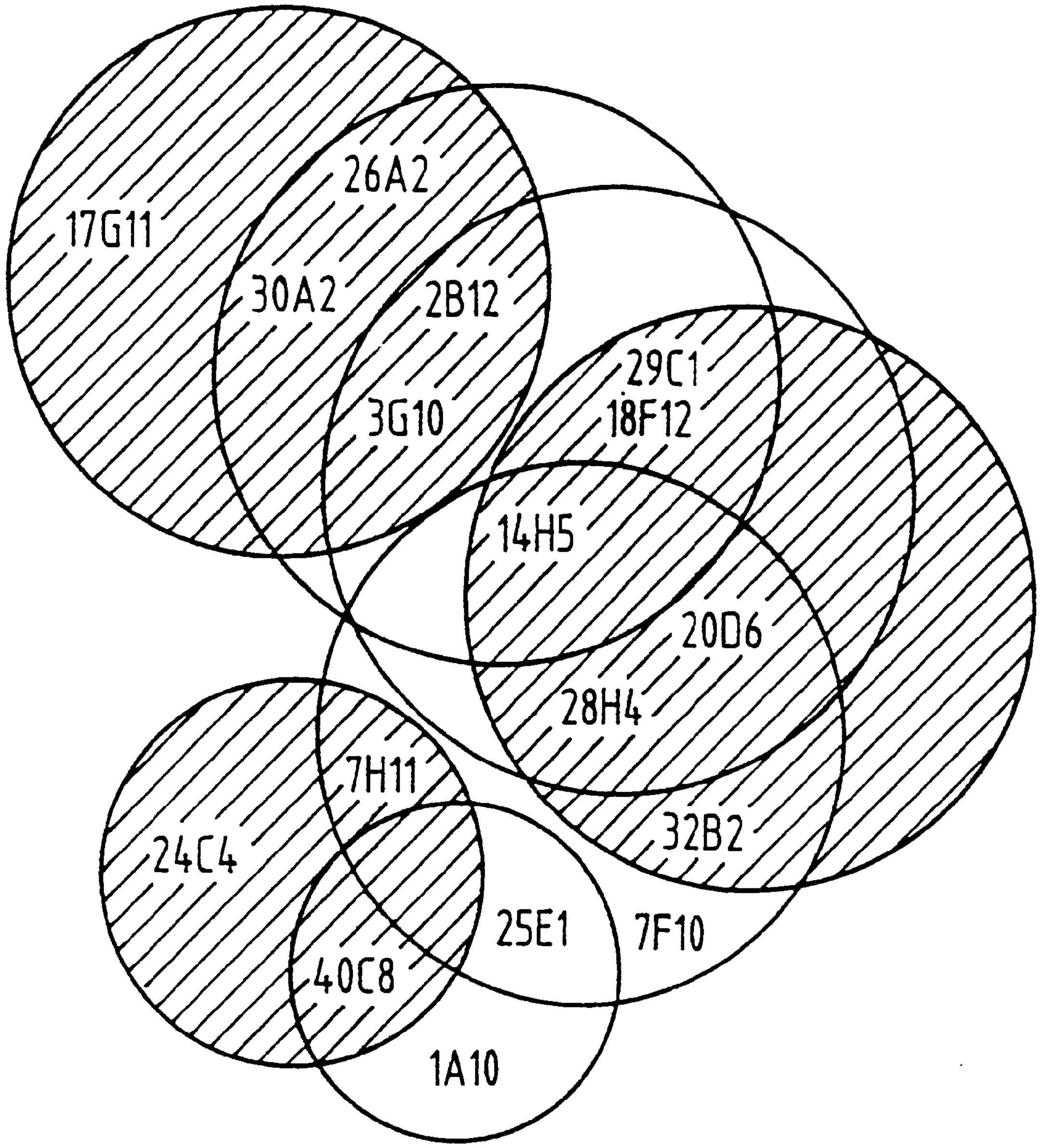
FIG. 2 shows a schematic diagram of interrelationship among disclosed monoclonal antibodies.

In the above and the following the terms "derivatives", "mutants" and "variants" are used interchangeably U.S. Pat. No. 5,695,754, issued Dec. 9, 1997 is hereby incorporated by reference.

The present invention will be demonstrated in more detail in the following examples, that are however not intended to be limiting to the scope of the invention. Based on the present invention several variants and improvements will be obvious for the person skilled in the art. Thus random mutagenesis is likely to generate alternative mutants with reduced immunogenicity and possibly increased functional activity, whereas mutagenesis of other amino acids may yield other variants with reduced immunogenicity.

EXAMPLE 1

Epitope mapping of wild-type staphylokinase

The epitope specificity of a panel of 15 murine MAbs (22) raised against wild-type SakSTAR was determined by real-time biospecific interaction analysis (BIA) with the BIAcore instrument (Pharmacia, Biosensor AB, Uppsala, Sweden). The MAbs were immobilized on the surface of the Sencor Chip CM5 with the Amine Coupling Kit (Pharmacia Biosensor AB) as recommended by the manufacturer (25). Immobilization was performed from protein solutions at a concentration of 20 μg/mL in 10 mmol/L sodium acetate at pH 5.0 at a flow rate of 5 μL/min during 6 minutes. This resulted in covalent attachment of 5,000 to 10,000 resonance unit (RU) of antibody (corresponding to 0.035 to 0.07 $pmol/mm^2$). The SakSTAR solutions were passed by continuous flow at 20° C. past the sensor surface. At least four concentrations of each analyte (range, 50 nmol/L to 50 μmol/L) in 10 mmol/L HEPES, 3.4 mmol/L EDTA, 0.15 mol/L NaCl, and 0.005% Surfactant P20, pH 7.2, were injected at a flow rate of 5 μL/min during 6 minutes in the association phase. Then sample was replaced by buffer, also at a flow rate of 5 μL/min during 6 minutes. After each cycle, the surface of the sensor chip was regenerated by injection of 5 μL of 15 mmol/L HCl. Apparent association ($k_{ass}$) and apparent dissociation ($k_{diss}$) rate constants were derived from the sensorgrams as described in detail elsewhere (26).

Determination of the equilibrium association constants for the binding of wild-type and variant SakSTAR to insolubilized MAbs (Table 1) yielded apparent association constants of $10^7$ to $10^8$ $(mol/L)^{-1}$, which are one to two orders of magnitude lower than the apparent association constants previously obtained for the binding of these MAbs to insolubilized wild-type SakSTAR (22). If the MAbs instead of the SakSTAR variants are insolubilized, avidity effects of the bivalent MAbs are indeed avoided. These present values are indeed in better agreement with known association constants of Mabs, and therefore this "reversed" procedure was used throughout the present invention.

In table 1 the column indicated with "Compound" states the various staphylokinase derivatives, the column "Substituted amino acids" identifies the modified wild-type residues, their position in the sequence and their substituted amino acid, and the column "Spec. Act." indicates the specific activity in Home Units. Indications "17G11", "26A2" etc. refer to monoclonal antibodies binding to the indicated epitopes I, II, and III (22). Epitope I is recognized by the antibody cluster 17G11, 26A2, 30A2, 2B12 and 3G10, whereas epitope II is recognized by the antibody cluster 18F12, 14H5, 28H4, 32B2 and 7F10, and epitope III by the antibody cluster 7H11, 25E1, 40C8, 24C4 and 1A10. Deposit of certain of these hybridomas have been made in the Belgian Coordinated Collections of Microorganisms (BCCM), Laboratorium voor Moleculaire Biologie-Plasmidencollectie (LMBP), Universiteit Gent. K. L. Ledeganckstraat 35, B-9000 Gent, Belgium. The accession numbers for the hybridomas are as follows: 28H4, LMBP1629CB; 18F12, LMBP1628CB; 3G10, LMBP1632CB; 30A2, LMBP1630CB; 17G11, LMBP1635CB; 1A10, LMBP1634CB; 24C4, LMBP1633CB; 7H11, LMBP1627CB AND 32B2, LMBP1631CB.

EXAMPLE 2

Construction and epitope mapping, with murine monoclonal antibodies, of "alanine-to-wild-type" reversal variants of "charged-cluster-to-alanine" mutants of staphylokinase As stated above, wild-type staphylokinase (SakSTAR variant (9)) contains three non-overlapping immunodominant epitopes, two of which can be eliminated by specific site-directed substitution of clusters of two (K35A,E38A or E80A,D82A) or three (K74A,E75A,R77A) charged amino acids with Ala (22). The combination mutants SakSTAR (K35A,E38A,K74A,E75A,R77A) in which Lys35, Glu38, Lys74, Glu75 and Arg77, and SakSTAR(K74A,E75A, R77A,E80A,D82A) in which Lys74, Glu75, Arg77, Glu80 and Asp82 were substituted with Ala (previously identified as SakSTAR.M3.8 and SakSTAR.M8.9, respectively (22)), were found to have a reduced reactivity with murine monoclonal antibodies against two of the three immunodominant epitopes and to absorb on average only ⅔ of the neutralizing antibodies elicited in 16 patients by treatment with wild-type SakSTAR (22). These mutants also induced less antibody formation than wild-type SakSTAR in rabbit and baboon models, and in patients with peripheral arterial occlusion (22). However, their specific activities were reduced to approximately 50% of that of wild-type SakSTAR, which would be of some concern with respect to the clinical use of these compounds.

In an effort to improve the activity and stability without loss of the reduced antibody recognition, the effect of a systematic reversal of one or more of these substituted amino acids to the wild-type residues was studied. Fourteen new mutants were constructed, purified and characterized in terms of specific activity, reactivity with the panel of murine monoclonal antibodies (Table 1), and absorption of antibodies from plasma of patients treated with wild-type SakSTAR (Table 2). The present example thus focusses on reversal from alanine to the wild-type residue of one or more of the seven amino acids of SakSTAR listed above i.e. K35, E38, K74, E75, R77, E80 and D82. The mutants are identified by the substituted amino acids in the order of their sequence in the molecule, with addition in subscript of those sequence numbers required to avoid ambiguity. For example, SakSTAR(K35A,E38A,K74A,E75A,R77A) is identified as SakSTAR(KEKER) and SakSTAR(K74A,E75A,R77A) as SakSTAR($K_{74}$ ER).

The source of all reagents used in the present study has previously been reported (22). Restriction enzymes were purchased from Pharmacia, Uppsala, Sweden or Boehringer Mannheim (Mannheim, Germany). T4 DNA ligase, Klenow Fragment of *E. coli* DNA polymerase I and alkaline phosphatase were obtained from Boehringer Mannheim. Enzyme reactions were performed using the conditions suggested by the suppliers. Plasmid DNA was isolated using a QIAGEN-purification protocol (provided by Westburg, Leusden, The Netherlands). pMEX.602sakB (i.e. pMEX.SakSTAR) was constructed as described elsewhere (23). SakSTAR, SakSTAR($KE_{38}$), SakSTAR($K_{74}$ER), SakSTAR($E_{80}$D), SakSTAR(KEKER) and SakSTAR($K_{74}$ERED) were produced and purified as described elsewhere (22). Transformations of *E. coli* were performed utilizing the calcium phosphate procedure. DNA sequencing was performed using the dideoxy chain termination reaction method and the Automated Laser fluorescent A.L.F.™ (Pharmacia). The chromogenic substrate (S2403) L-Pyroglutamyl-L-phenylalanyl-L-lysine-P-nitroanaline hydrochloride was purchased from Chromogenix (Belgium). $^{125}$I-labeled fibrinogen was purchased from Amersham (UK). All other methods used in the present example have been previously described (22,27).

The plasmids encoding SakSTAR($KEKE_{75}$), SakSTAR (EER), SakSTAR($EE_{75}$), SakSTAR($K_{35}E_{75}$R), SakSTAR ($K_{35}E_{75}$), SakSTAR($E_{80}$), SakSTAR(D), SakSTAR($E_{75}$D), SakSTAR($K_{74}$) and SakSTAR($E_{75}$) were constructed by the spliced overlap extension polymerase chain reaction (SOE-PCR) (24), using Vent DNA polymerase (New England Biolabs, Leusden, The Netherlands), and available or generated SakSTAR variants as template. Two fragments were amplified by PCR, the first one starting from the 5' end of the staphylokinase gene with primer 5'-CAGGAAA-CAGAATTCAGGAG-3' to the region to be mutagenized (forward primer SEQ ID NO:1), the second one from the same region (backward primer SEQ ID NO:2) to the 3' end of the staphylokinase gene with primer 5'-CAAAACAGCCAAGCTTCATTCATTCAGC-3'. The forward and backward primers shared an overlap of around 24 bp (primers not shown). The two purified fragments were then assembled together in a new primeness PCR using Taq polymerase (Boehringer Mannheim). After 7 cycles (1 min at 94° C., 1 min at 70° C.), the extended product was reamplified by adding the 5' and 3' end primers (see above) to the PCR reaction and by cycling 25 times (1 min at 94° C., 1 min 55° C., 1 min at 72° C.). The final product was purified, digested with EcoRI and HindIII and cloned into the corresponding sites of pMEX602sakB.

The plasmid encoding SakSTAR(EKER) was assembled by digestion of pMEX602sakB and pMEX.SakSTAR (KEKER) with Bpm I which cuts between the codons for K35 and E38 of SakSTAR, and ligation of the required fragments. The plasmid encoding SakSTAR(KKER) was constructed by digestion of pMEX.SakSTAR(KEKER) and pMEX.SakSTAR($K_{74}$ER) with Bpm I and religation of the required fragments. The plasmids encoding SakSTAR (KEER) and SakSTAR(KEKR) were constructed by two PCR using pMEX.SakSTAR(KEKER) as template, followed by restriction ligation and recloning into pMEX602sakB.

Analytical purification of SakSTAR variants

The SakSTAR variants were expressed and purified, as described below, from transformed *E coli* WK6 grown either in LB medium [SakSTAR(EKER), SakSTAR($K_{74}$), SakSTAR($E_{75}$) and SakSTAR($E_{75}$D)], or in terrific broth (TB) (28) medium [SakSTAR(KKER), SakSTAR(KEER), SakSTAR(KEKR), SakSTAR($KEKE_{75}$), SakSTAR(EER), SakSTAR($EE_{75}$), SakSTAR($K_{35}E_{75}$), SakSTAR($K_{35}$ $E_{75}$), SakSTAR($E_{80}$), and SakSTAR(D)].

For derivatives produced in LB medium, a 20 ml aliquot of an overnight saturated culture was used to inoculate a 2 liter volume (in a 5 liter flask) of LB medium containing 100 μg/ml ampicillin. After 3 hours incubation at 37° C., IPTG (200 μM) was added to induce expression from the tac promoter. The production phase was allowed to proceed for 4 hours, after which the cells were pelleted by centrifugation at 4,000 rpm for 20 min, resuspended in 1/20 volume (100 ml) of 0.01 M phosphate buffer pH 6.5 and disrupted by sonication at 0° C. Cell debris were removed by centrifugation for 20 min at 20,000 rpm and the supernatant, containing the cytosolic soluble protein fraction, was stored at −20° C. until purification.

For the derivatives produced in TB medium, a 4 ml aliquot of an overnight saturated culture in LB medium was used to inoculate a 2 liter culture (in a 5 liter flask) in terrific broth containing 100 μg/ml ampicillin. The culture was grown with vigorous aeration for 20 hours at 30° C. The cells were pelleted by centrifugation, resuspended in 1/10 volume (200 ml) of 0.01 M phosphate buffer pH 6.5 and disrupted by sonication at 0° C. The suspension was then centrifuged for 20 min at 20,000 rpm and the supernatant was stored at −20° C. until purification.

Cleared cell lysates containing the SakSTAR variants were subjected to chromatography on a 1.6×6 cm column at SP-Sephadex, followed by chromatography on a 1.6×5 cm column of Q-Sepharose (variants SakSTAR(EKER), SakSTAR(KKER), SakSTAR(KEER), SakSTAR(KEKR) and SakSTAR($KEKE_{75}$)) or by chromatography on a 1.6×6 cm column phenyl-Sepharose (variants SakSTAR(EER), SakSTAR($EE_{75}$), SakSTAR($K_{35}E_{75}$R), SakSTAR($K_{35}E_{75}$), SakSTAR($K_{74}$), SakSTAR($E_{75}$), SakSTAR($E_{80}$), SakSTAR (D) and SakSTAR($E_{75}$D)). The SakSTAR containing fractions, localized by SDS-gel electrophoresis, were pooled for further analysis.

Protein concentrations were determined according to Bradford (29). The fibrinolytic activities of SakSTAR solutions were determined with a chromogenic substrate assay carried out in microtiters plates using a mixture of 80 μl SakSTAR solution and 100 μl Glu-plasminogen solution prepared as described elsewhere (30) (final concentration 0.5 mM). After incubation for 30 min at 37° C., generated plasmin was quantitated by addition of 30 μl S2403 (final concentration 1 μM) and measurement of the absorption at 405 nm. The activity was expressed in home units (HU) by comparison with an in-house standard (lot STAN5) which was assigned an activity of 100,000 HU per mg protein as determined by amino acid composition (7). SDS-PAGE was performed with the Phast System™ (Pharmacia, Uppsala, Sweden) using 10–15% gradient gels and Coomassie Brilliant blue staining. Reduction of the samples was performed by heating at 100° C. for 3 min in the presence of 1% SDS and 1% dithioerythritol. The fibrinolytic activities of the different SakSTAR mutants determined with the chromogenic substrate assay are summarized in table 1. In agreement with previous observations (22), SakSTAR($K_{74}$ER) did not react with 4 of the 5 MAbs recognizing epitope I, whereas SakSTAR($KE_{38}$) did not react with 3 of the 5 and SakSTAR ($E_{80}$D) not with the 4 of the 5 Mabs recognizing epitope III. These reduced reactivities were additive in SakSTAR (KEKER) and in SakSTAR($K_{74}$ERED). The reduced reactivity of SakSTAR($K_{74}$ER) was fully maintained in SakSTAR($KEKE_{75}$) and in SakSTAR($K_{35}E_{75}$R), largely in SakSTAR(KEER), SakSTAR(EER), SakSTAR($EE_{75}$) and SakSTAR($E_{75}$), but much less in SakSTAR(KEKR) and SakSTAR($K_{74}$), indicating that E75 is the main contributor to the binding of the 4 Mabs recognizing epitope I to SakSTAR. However, surprisingly, binding of epitope I antibodies to SakSTAR($E_{75}$D) was normal in two independent preparations from expression plasmids with confirmed DNA sequences. The reduced reactivity of the 3 MAbs of epitope III with SakSTAR($KE_{38}$) required both K35 and E38, as demonstrated with SakSTAR(EKER) and SakSTAR (KKER), with SakSTAR($EE_{75}$) and SakSTAR($K_{35}E_{75}$) and with SakSTAR(EER) and SakSTAR($K_{35}E_{75}$R). The reduced reactivity of the 4 MAbs of cluster III with SakSTAR($E_{80}$D) was maintained in SakSTAR(D) but not in SakSTAR($E_{80}$).

EXAMPLE 3

Adsorption with wild-type and with "alanine-to-wild-type" reversal variants of "charged-cluster-to-alanine" staphylokinase mutants of antibodies, elicited in patients by treatment with wild-type SakSTAR Plasma samples from 16 patients with acute myocardial infarction, obtained several weeks after treatment with SakSTAR (4,31) were used. The staphylokinase-neutralizing activity in these samples was determined as follows. Increasing concentrations of wild-type or variant SakSTAR (50 μl volumes containing 0.2 to 1000 μg/ml) were added to a mixture of 300 μl citrated human plasma and 50 μl buffer or test plasma, immediately followed by addition of 100 μl of a mixture containing thrombin (50 NIH units/ml) and $CaCl_2$ (25 mM). The plasma clot lysis time was measured and plotted against the concentration of SakSTAR moiety. From this curve the concentration of staphylokinase moiety that produced complete clot lysis in 20 min was determined. The neutralizing activity titer was determined as the difference between the test plasma and buffer values and was expressed in μg per ml test plasma. The results of the individual patients have been reported elsewhere (22). For the present invention, three plasma pools were made, one from 10 patients from whom sufficient residual plasma was available, one from three patients that absorbed less than 50% of the antibodies with SakSTAR(KEKER) (Subpool B) and one from three patients that absorbed >90% of the antibodies with SakSTAR(KEKER) (Subpool C).

These plasma pools were diluted (1/30 to 1/200) until their binding to SakSTAR substituted chips in the BIAcore instrument amounted to approximately 2000 RU. From this dilution a calibration curve for antibody binding was constructed using further serial two-fold dilutions. The plasma pools were absorbed for 10 min with 100 nM of the SakSTAR variants, and residual binding to immobilized SakSTAR was determined. Residual binding was expressed in percent of unabsorbed plasma, using the calibration curve.

The results are summarized in Table 2. Whereas wild-type SakSTAR absorbed more than 95% of the binding antibodies from pooled plasma of the 10 patients, incomplete absorption (<60%) was observed with SakSTAR($K_{74}$ER), SakSTAR(KEKER), SakSTAR(EKER), SakSTAR(KKER), SakSTAR(KEKR), SakSTAR($KEKE_{75}$), SakSTAR($K_{74}$) and SakSTAR($K_{74}$ERED) but absorption was nearly complete with SakSTAR($KE_{38}$), SakSTAR(KEER), SakSTAR (EER), SakSTAR($E_{38}E_{75}$), SakSTAR($K_{35}E_{75}$R), SakSTAR ($E_{80}$D), SakSTAR($E_{80}$) and SakSTAR(D). These results, surprisingly, demonstrate that approximately 40% of the antibodies elicited in patients by treatment with wild-type SakSTAR depend on K74 for their binding (Table 2). Absorption with pooled plasma from 3 patients from which <50% of the antibodies were absorbed with SakSTAR (KEKER) (Subpool B) confirmed the predominant role of K74 for antibody recognition. As expected, absorption with pooled plasma from 3 patients from which >95% of the antibodies were absorbed with SakSTAR(KEKER) (Subpool C) was nearly complete with all variants tested.

EXAMPLE 4

Construction and epitope mapping, with murine monoclonal antibodies, of site-specific mutants of staphylokinase Site-directed mutagenesis was applied to residues other than "charged amino acids" in order to identify i) additional residues belonging to epitopes I and III identified with the panel of murine Mabs ii) amino acids determining adsorption to antiserum from immunized patients and ii) key residues recognized by the monoclonal antibody cluster specific for epitope II (as defined in example 1 above). Since functional epitopes generally comprise more than one amino acid residue critical for antibody binding, identification of additional residues in these epitopes could fuel the construction of new combination derivatives displaying a lower antigenic profile, while keeping the specific activity and the temperature stability of wild-type staphylokinase.

In this example, the construction and characterization of SakSTAR variants in which one or at most two amino acids (adjacent or in close vicinity) were mutated to alanine is described. We show also that other types of substitution at key residues for binding to murine monoclonal antibodies and/or at critical residues for adsorption to antiserum from immunized patients can be identified, while keeping the modified antigenic profile. In addition, for some key amino acids, mutation into other residues than in alanine is preferable to maintain the specific activity of the variants.

The mutants described under this example are listed in tables 3 and 4. These variants were expressed in *E. coli,* purified and characterized in terms of specific activity, reactivity with the panel of murine monoclonal antibodies (Table 3), and absorption of antibodies from plasma of patients treated with wild-type SakSTAR (Table 4).

The source of all reagents used in the present study has previously been reported (22), or is specified below. The template vector for mutagenesis, pMEX602sakB (i.e. pMEX.SakSTAR), has been described elsewhere (23). The construction of the variant SakSTAR(K74) is described above (example 2). Restriction and modification enzymes were purchased from New England Biolabs (Leusden, The Netherlands), Boehringer Mannheim (Mannheim, Germany) or Pharmacia (Uppsala, Sweden). The enzymatic reactions were performed according to the supplier recommendation. The mutagenic oligonucleotides and primers were obtained from Eurogentec (Seraing, Belgium). Plasmid DNA was isolated using a purification kit from Qiagen (Hilden, Germany), as recommended. Transformation-competent *E. coli* cells were prepared by the well-known calcium phosphate procedure. Nucleotide sequence determination was performed on double strand plasmid DNA with the dideoxy chain termination method, using the T7 sequencing kit (Pharmacia, Uppsala, Sweden). Polymerase chain reactions (PCR) were performed using Taq polymerase from Boehringer Mannheim (Mannheim, Germany). The recombinant DNA methods required to construct the variants described in this example are well established.

The variants SakSTAR.M27, SakSTAR.M46, SakSTAR.M48, SakSTAR.M44, SakSTAR.M53, SakSTAR.M54, SakSTAR.M55, SakSTAR.M67 and SakSTAR.M56 were constructed with the Chameleon Double-Stranded Site-Directed Mutagenesis kit from Stratagene (La Jolla, USA), using the pMEX.SakSTAR vector as template, and following instructions of the supplier. The mutagenic oligonucleotides (not shown) were used in combination with the selection-primer LY34 (SEQ ID NO:3) 5' CAAAACAGCCGAGCTTCATTCATTCAGC, which destroys the unique HindIII site located 3' to the staphylokinase encoding gene into pMEX.SakSTAR and allows to counter-select the non-mutant progeny by a HindIII digestion. The deletion of the HindIII site was in most case correlated with the presence of the desired mutation introduced by the mutagenic oligonucleotide. The variants SakSTAR.M58, in which Ile133 is mutated in alanine, was constructed by performing a polymerase chain reaction on the pMEX.SakSTAR plasmid using the primer 818A (SEQ ID NO:1) located at the 5' end of the sakSTAR gene (5' CAGGAAACAGAATTCAGGAG ) and the mutagenic primer LY58 (SEQ ID NO:4) (5' TTCAGCATGCTGCAGTTATTTCTTTTCTGCAACAACCTTGG). The amplified product (30 cycles: 30 sec at 94° C., 30 sec at 50° C., 30 sec at 72° C.) was purified, digested with EcoRI and PstI, and ligated into the corresponding sites of pMEX-SakSTAR.

The variants SakSTAR.M57, SakSTAR.M127 and SakSTAR.M137 were constructed by performing a polymerase chain reaction using the primer 818A located at the 5' end of the sakSTAR gene and mutagenic primers (not shown). The amplified product (30 cycles: 1 sec at 94° C., 1 sec at 50° C., 10 sec at 72° C.) was purified, digested with EcoRI and StyI, and ligated into the corresponding sites of pMEXSakSTAR. The variant SakSTAR.M2426 was constructed by performing two consecutive PCR reactions (30 cycles: : 30 sec at 94° C., 30 sec at 50° C., 30 sec at 72° C.). In the first reaction, a fragment of pMEX.SaksSTAR was amplified with the primers 818A and a mutagenic primer. This amplified fragment was then used as template in a second PCR reaction with a mutagenic primer in order to further elongate the fragment downstream of the StyI site present in the sakSTAR gene (corresponding to amino acids 130–131 of SakSTAR). The resulting product was digested with EcoRI and StyI, and ligated into the corresponding sites of pMEX-SakSTAR.

The plasmids encoding all the other variants listed in tables 3 and 4 were constructed by the spliced overlap extension polymerase chain reaction (SOE-PCR)(24) using pMEX.SakSTAR or available plasmids encoding SakSTAR variants as template. Two fragments were amplified by PCR (30 cycles: 1 sec at 94° C., 1 sec at 50° C., 10 sec at 72° C.), the first one starting from the 5' end (primer 818A) of the staphylokinase gene to the region to be mutagenized (forward primer), the second one from this same region (backward primer) to the 3' end of the gene with primer 818D (SEQ ID NO:2) (5' CAAACAGCCAAGCTTCATTCATTCAGC). the forward and backward primers shared an overlap of around 24 bp (primers not shown). The two purified fragments were then assembled together in a second PCR reaction with the external primers 818A and 818D (30 cycles: 1 sec at 94° C., 1 sec at 50° C., 10 sec at 72° C.). The amplified product from this final reaction was purified, digested with EcoRI and HindIII and ligated into the corresponding site of pMEX.SakSTAR.

For each construction, the sequence of the variant was confirmed by sequencing the entire SakSTAR coding region.

Analytical purification of SakSTAR variants

The SakSTAR variants were expressed and purified, as described below, from transformed *E. coli* grown in terrific broth (TB) medium. A 4 ml aliquot of an overnight saturated culture in LB medium was used to inoculate a 1 to 2 liter culture (in 5 liter flask) in terrific broth supplemented with 100 ug/ml ampicillin. The culture was incubated with vigorous aeration and at 30° C. After about 16 hours incubation, IPTG (200 uM) was added to the culture to induce expression from the tac promoter. After 3 hours induction, the cells were pelleted by centrifugation at 4,000 rpm for 20 min., resuspended in 1/10 volume of 0.01 M phosphate buffer pH 6–6.5 and disrupted by sonication at 0° C. The suspension was centrifuged for 20 min at 20,000 rpm and the supernatant was stored at 4° C. or at −20° C. until purification. The material was purified essentially as described above (Example 2): cleared cell lysates containing the SakSTAR variants were subjected to chromatography on a 1.6×5 cm column of SP-Sephadex, followed by chromatography on a 1.6×8 cm column of phenyl-Sepharose. The SakSTAR containing fractions, localized by SDS-gel electrophoresis, were pooled for further analysis.

Physiochemical and biochemical analysis

Protein concentrations were determined according to Bradford (29). SDS-PAGE was performed with the Phast System™ (Pharmacia, Uppsala, Sweden) using 10–15% gradient gels and Coomassie Brillant blue staining. Reduction of the samples was performed by heating at 10° C. for 3 min in the presence of 1% SDS and 1% dithioerythritol. The fibrinolytic activities of SakSTAR solutions were determined with a chromogenic substrate assay carried out in microtiter plates using a mixture of 80 ul SakSTAR solution and 100 ul Glu-plasminogen solution (final concentration 0.5 mM). After incubation for 30 min at 37° C., generated plasmin was quantitated by addition of 30 ul S2403 (final concentration 100 uM) and measurement of the absorption at 405 nm. The activity was expressed in home units (HU) by comparison with an in-house standard (lot STAN5) which was assigned an activity of 100,000 HU per mg protein as determined by amino acid composition (7). The specific activity of the different SakSTAR variants are summarized in tables 3 and 4.

Reactivity of SakSTAR variants with a panel of murine monoclonal antibodies

The methodology used to determine the reactivity of the SakSTAR variants with a panel of murine monoclonal antibodies was described in example 1 above.

In the present example, sixty-five mutants were evaluated in detail, together with wild-type staphylokinase. The results are summarized in table 3 (the layout of this table corresponds to the layout of table 1, as described in example 1). Apparent association constants at least 10-fold lower than those of wild-type staphylokinase were considered as significant and are indicated in bold type in the table.

Thirty-five variants displayed a modified recognition profile by the mouse monoclonal antibodies (mMAbs) compared to SakSTAR. SakSTAR.M3031 [SakSTAR(Y73A)] is not recognized by 3 mMAbs of cluster I; SakSTAR.M8586 [SakSTAR(W66A)] is not recognized by 5 mMAbs of cluster I; SakSTAR.M128129 [SakSTAR(L116A,S117A)] is not recognized by 2 mMAbs of cluster II; SakSTAR.M5960 [SakSTAR(H43A)] is not recognized by 3 mMAbs of cluster II; SakSTAR.M7576 [SakSTAR(V45A)] is not recognized by 3 mMAbs of cluster II; and SakSTAR.M9596 [SakSTAR (V32A)] is not recognized by 4 mMAbs of cluster III; in these variants, uncharged residue(s) were modified in alanine.

Alanine does not constitute the only possible substituent for a particular residue. For example, variants SakSTAR.M103104 and SakSTAR.M105106, with Gly36 modified respectively in Arg and in Lys, displayed a similarly altered antigenic profile (i.e., not recognized by 3 mMAbs of cluster III). Likewise, mutation of residue His43 in Ala (SakSTAR.M5960) or in Arg (SakSTAR.M6162) resulted in a similarly modified reactivity with the monoclonal antibody panel (not recognized by 3 mMAbs of cluster II). However, the specific activity of these variants, 69,000 and 120,000 respectively, indicated that Arg represents a prefered substitution for His43.

Another aspect of this invention is illustrated by the evaluation of six other variants, in which residue Tyr73 was mutated respectively in Ala, Phe, Trp, Ser, His and Leu (Table 3). SakSTAR.M145146a [SakSTAR(Y73F)] and SakSTAR.M171172 [SakSTAR(Y73W)] reacted as wild-type SakSTAR with the monoclonal antibody panel, while the antigenic reactivities of the four other variants were altered to different levels depending on the introduced residue: SakSTAR.M145146c [SakSTAR(Y73S)] was not recognized by 1 mMAb of cluster I; SakSTAR.M169170 [SakSTAR(Y73H)] was not recognized by 2 mMAbs of cluster l; SakSTAR.M3031 [SakSTAR(Y73A)] was not recognized by 3 mMAbs of cluster I; and SakSTAR.M145146b [SakSTAR(Y73L)] was not recognized by 4 mMAbs of cluster I.

EXAMPLE 5

Adsorption with wild-type and site-specific staphylokinase variants of antibodies, elicited in patients by treatment with SakSTAR For the present example, the three plasma pools prepared from 10 patients, as described in example 3 were used. The methodology used to evaluate the absorption with wild-type staphylokinase and with 65 SakSTAR variants, of antibodies elicited in patients treated with SakSTAR, is described in detail in example 3. The results are summarized in Table 4. Whereas wild-type SakSTAR and most of the variants analyzed in this example absorbed more than 95% of the binding antibodies from pooled plasma of the 10 patients, incomplete absorption (<60%) was observed with SakSTAR.M3031, in which Tyr73 is substitued with Ala, and with the combined variants SakSTAR.M7980 with Y73A,K74A, SakSTAR.M8990 with Y73F,K74A and SakSTAR.M103104+ with G36R,K74A. The predominant role of Lys74 for antibody recognition has been demonstrated previously (see example 3). The present results suggest that Tyr73 participates to the same major epitope as Lys74, or, alternatively, that substitution at Tyr73 may indirectly induce a structural modification of the "K74-epitope". Absorption with pooled plasma from 3 patients from which >95% of the antibodies were absorbed with SakSTAR (KEKER) (Subpool C, see example 3) was nearly complete with most variants tested. However, incomplete absorption was observed with the variants SakSTAR.M103104 [SakSTAR(G36R)] and SakSTAR.M105106 [SakSTAR(G36K)] (<70%), and with the combination variant SakSTAR.M103104+[SakSTAR (G36R,K74A)] (<60%). This combination variant absorbed also <40% of the antibodies from Subpool B, and had a specific activity of 65,000 HU/mg (>50% of wild-type SakSTAR).

EXAMPLE 6

Identification of selected variants of staphylokinase with more than 50% residual specific activity, a more than 10-fold reduced binding to murine MAbs of one of the immunodominant epitopes and a less than 80% adsorption of pooled human antibodies elicited in patients by treatment with wild-type SakSTAR.

Five of the variants constructed and characterized in the present study combined the property of a residual specific activity of ≧50 percent of that of wild-type SakSTAR with a ≧10-fold reduced reactivity with one or more of the murine monoclonal antibodies and/or with less than 80 percent absorption with one of the subpools of antisera obtained from patients treated with wild-type SakSTAR. The results are summarized in Table 5.

In the plasma pool from 10 patients treated with SakSTAR for acute myocardial infarction, the elicited antibodies were only adsorbed for approximately 50% by SakSTAR (KEKER) and SakSTAR($K_{74}$ERED). This reduced reactivity could be fully ascribed to the K74,E75,R77 epitope, with little contribution by the K35,E38 or E80,D82 epitopes. Furthermore, the reduced antibody recognition was largely maintained in SakSTAR($K_{74}$), which had an intact specific activity and clearly the best activity/antigenicity ratio in man of all "alanine to wild-type reversal" variants studied. In subpool B, containing plasma from 3 patients from which SakSTAR(KEKER) adsorbed less than 50% of the antibodies elicited by SakSTAR treatment, similar although more pronounced altered antibody recognition patterns were observed with the SakSTAR variants. As expected, subpool C, prepared from plasma of 3 patients from which SakSTAR (KEKER) adsorbed over 95%, similar antibody recognition patterns were observed with all SakSTAR variants studied.

The most surprising observation in man, which could not have been predicted nor extrapolated from results obtained in mice, is that only one of these 7 amino acids, namely K74, is responsible for most of the reduction in antibody recognition of the SakSTAR(KEKER) and SakSTAR($K_{74}$ERED) variants, although a subgroup of patients (Subpool C) did not develop significant levels of antibodies against these epitopes. Alternatively, SakSTAR(G36K) and SakSTAR (G36R) combined an intact specific activity with reduced murine antibody binding to epitope III and, importantly, reduced absorption of antibodies from subpool C. The combination mutant SakSTAR(G36R,K74A) combined the reduced antibody recognition patterns of the parent variants, with maintenance of a residual specific activity of 50 percent of that of wild-type SakSTAR.

EXAMPLE 7

Comparative thrombolytic efficacy and immunogenicity of SakSTAR(K74A,E75A,R77A) and SakSTAR(K74A) versus SakSTAR in patients with peripheral arterial occlusion A 12 to 24 liter culture (in 2 liter batches) of the variants SakSTAR(K74A,E75A,R77A) herinafter called SakSTAR ($K_{74}$ER), or of SakSTAR(K74A), hereinafter called SakSTAR($K_{74}$) was grown and IPTG-induced in LB medium supplemented with 100 μg/ml ampicillin, pelleted, resuspended, disrupted by sonication and cleared as described above. The compounds were purified by chromatography on a 5×20 cm column of SP-Sephadex, a 5×10 cm column of Q-Sepharose and/or a 5×cm column of phenyl-Sepharose using buffer systems described elsewhere (22, 23). The materials were then gel filtered on sterilized Superdex 75 to further reduce their endotoxin content. The SakSTAR variant containing fractions were pooled, the protein concentration was adjusted to 1 mg/ml and the material sterilized by filtration through a 0.22 μm Millipore filter. The methodology used to determine specific activity is described above (22).

Staphylokinase-neutralizing activity in plasma was determined as described above. Quantitation of antigen-specific IgG and IgM antibodies was performed using enzyme-linked immunosorbent assays in polystyrene microtiter plates essentialy as described previously (22). In the IgG assays, dilution curves of affinospecific anti-SakSTAR IgG antibodies were included on each plate. These antibodies were isolated from plasma obtained from 3 patients, after thrombolytic therapy with wild-type SakSTAR, by chromatography on protein A-Sepharose and on insolubilized SakSTAR, and elution of bound antibodies with 0.1 M glycine-HCl, pH 2.8. The purity of the IgG preparation was confirmed by sodium dodecylsulfate polyacrylamide gel electrophoresis. In the IgM assays, titers defined as the plasma dilution giving an absorbancy at 492 nm equivalent to that of a 1/640 dilution of pooled plasma were determined and compared with the titer of baseline samples before treatment (median value 1/410, interquartile range 1/120–1/700).

Wild-type SakSTAR or the variants SakSTAR($K_{74}$) or SakSTAR($K_{74}$ER) were administered intra-arterially at or in the proximal end of the occlusive thrombus as a bolus of 2 mg followed by an infusion of 1 mg/hr (reduced overnight in some patients to 0.5 mg/hr) in groups of 6 to 12 patients with angiographically documented occlusion of a peripheral artery or bypass graft of less than 120 days duration. Patients were studied after giving informed consent, and the protocol was approved by the Human Studies Committee of the University of Leuven. Inclusion and exclusion criteria, conjunctive antithrombotic treatment (including continuous intravenous heparin) and the study protocol were essentially as previously described (22).

Relevant baseline characteristics of the individual patients are shown in Table 6. The majority of PAO were at the femoropopliteal level. Two iliac stent and 8 graft occlusions were included. Eight patients presented with incapacitating claudication, 5 with chronic ischemic rest pain, 7 with subacute ischemia and 7 with acute ischemia. One patient (POE) who had 2 years previously been treated with SakSTAR was included in the SakSTAR($K_{74}$) group. This patient was not included in the statistical analyses of Tables 6, 7 and 8.

Table 7 summarizes the individual treatment and outcome. Intra-arterial infusion, at a dose of 6.0 to 25 mg and a duration of 4.0 to 23 hrs, induced complete recanalization in 24 patients and partial recanalization in 3. Complementary endovascular procedures (mainly PTA) were performed in 17 patients and complementary reconstructive vascular surgery following thrombolysis in 3. No patient underwent major amputation. Early recurrence of thrombosis after the end of the angiographic procedure occurred in 4 patients. Bleeding complications were absent or limited to mild to moderate hematoma formation at the angiographic puncture sites except for 5 patients who required transfusion (Table 7). Intracranial or visceral hemorrhage was not observed.

Circulating fibrinogen, plasminogen and $\alpha_2$-antiplasmin levels remained essentially unchanged during infusion of the SakSTAR moieties (Table 8), reflecting absolute fibrin specificity of these agents at the dosages used. Significant in vivo fibrin digestion occurred as evidenced by elevation of fibrin fragment D-dimer levels. Intra-arterial heparin therapy prolonged aPTT levels to a variable extent (Table 8).

Figure 3:
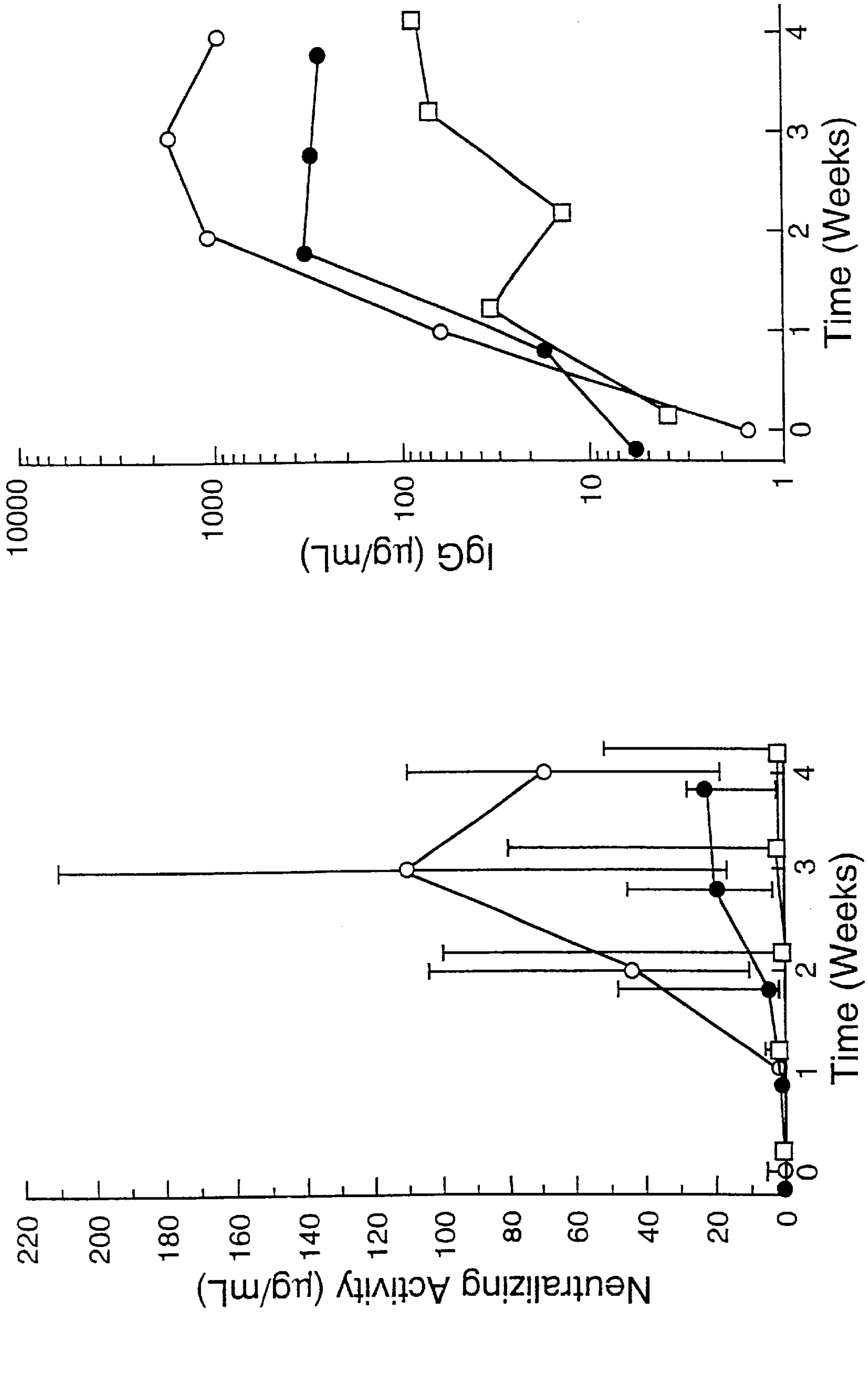
FIG. 3 are graphs showing a time course of neutralizing activities (left panel) and specific IgG against administered agent (right panel) following intra-arterial infusion of SakSTAR (open circles, N=9), SakSTAR($K_{74}$) (closed circles, N=11) or SakSTAR($K_{74}$ER) (open squares, n=6) in patients with peripheral arterial occlusion. The data represent median values and interquartile ranges, in μg/ml.

Antibody-related SakSTAR-, SakSTAR($K_{74}$)- and SakSTAR($K_{74}$ER)-neutralizing activity and anti-SakSTAR, anti-SakSTAR($K_{74}$) and anti-SakSTAR($K_{74}$ER) IgG, were low at baseline and during the first week after the infusion (FIG. 3). From the second week on, neutralizing activity levels increased to reach median values at 3 to 4 weeks of 20 μg SakSTAR($K_{74}$) and 2.4 μg SakSTAR($K_{74}$ER) neutralized per ml plasma in the patients treated with SakSTAR ($K_{74}$) and SakSTAR($K_{74}$ER), respectively, which is significantly lower than the median value of 93 μg wild-type SakSTAR neutralized per ml in the patients treated with SakSTAR ($p=0.024$ for differences between the three groups by Kruskal-Wallis analysis and $p=0.01$ and $p=0.036$, respectively, for variants vs wild-type by Mann-Whitney rank sum test). The levels of anti-SakSTAR($K_{74}$) and of anti-SakSTAR($K_{74}$ER) IgG increased to median values at 3 to 4 weeks of 270 and 82 μg/ml plasma in patients treated with SakSTAR($K_{74}$) and SakSTAR($K_{74}$ER) respectively, which is significantly lower than the median value of 1800 μg anti-SakSTAR per ml plasma in the patients treated with SakSTAR (($p=0.024$ for differences between the three groups by Kruskal-Wallis analysis and $p=0.007$ and 0.05, respectively, for variants versus wild-type by Mann-Whitney rank sum test).

The titers of anti-SakSTAR($K_{74}$) and of anti-SakSTAR ($K_{74}$ER) IgM increased from median baseline values of 1/460 and 1/410 to median values at 1 week of 1/510 and 1/450 in patients treated with SakSTAR($K_{74}$) and SakSTAR ($K_{74}$ER), respectively, which was not significantly different from the median values of 1/320 at baseline and 1/640 at week 1 in patients treated with SakSTAR. Corresponding values at 2 weeks were 1/590 and 1/550 in patients given SakSTAR($K_{74}$) and SakSTAR($K_{74}$ER), not significantly different from 1/930 with SakSTAR (data not shown).

The antibodies induced by treatment with SakSTAR were completely absorbed by SakSTAR but incompletely by SakSTAR($K_{74}$) and by SakSTAR($K_{74}$ER) confirming the immunogenicity of the K74,E75,R77 epitope and the dominant role of K74 in the binding of antibodies directed against this epitope. The antibodies induced by treatment with SakSTAR($K_{74}$) or SakSTAR($K_{74}$ER) were completely absorbed by SakSTAR, by SakSTAR($K_{74}$) and by SakSTAR ($K_{74}$ER), indicating that immunization was not due to neoepitopes generated by substitution of Lys74 with Ala, but to epitopes different from the K74,E75,R77 epitope.

In summary, the present experience illustrates that staphylokinase variants with reduced antibody induction but intact thrombolytic potency can be generated. To our knowledge, the present invention constitutes the first case in which a heterologous protein, with the use of protein engineering techniques, was rendered less immunogenic without reducing its biological activity.

REFERENCES

1. Lack CH: Staphylokinase: an activator of plasma protease. Nature 161: 559, 1948.
2. Lewis JH, Ferguson JH: A proteolytic enzyme system of the blood. III. Activation of dog serum profibrinolysin by staphylokinase. Am J Physiol 166: 594, 1951.
3. U.S. Pat No. 5,336,495 (issued Sep. 8, 1994).
4. Vanderschueren S, Barrios L, Kerdsinchai P, Van den Heuvel P, Hermans L, Vrolix M, De Man F, Benit E, Muyldermans L, Collen D, Van de Werf F: A randomized trial of recombinant staphylokinase versus alteplase for coronary artery patency in acute myocardial infarction. Circulation 92: 2044–2049, 1995.
5. Sako T, Sawaki S, Sakurai T, Ito S, Yoshizawa Y, Kondo I: Cloning and expression of the staphylokinase gene of *Staphylococcus aureus* in *Escherichia coli.* Molec Gen Genet 190: 271–277, 1983.
6. Behnke D, Gerlach D: Cloning and expression in *Escherichia coli, Bacillus subtilis,* and *Streptococcus sanguis* of a gene for staphylokinase—a bacterial plasminogen activator.

Molec Gen Genet 210: 528–534, 1987.
7. Collen D, Silence K, Demarsin E, De Mol M, Lijnen HR: Isolation and characterization of natural and recombinant staphylokinase. Fibrinolysis 6: 203–213, 1992.
8. Sako T, Tsuchida N: Nucleotide sequence of the staphylokinase gene from *Staphylococcus aureus*. Nucleic Acids Res 11: 7679–7693, 1983.
9. Collen D, Zhao ZA, Holvoet P, Marynen P: Primary structure and gene structure of staphylokinase. Fibrinolysis 6: 226–231, 1992.
10. Sakai M, Watanuki M, Matsuo O: Mechanism of fibrin-specific fibrinolysis by staphylokinase: participation of $\alpha_2$-plasmin inhibitor. Biochem Biophys Res Comm 162: 830–837, 1989.
11. Matsuo O, Okada K, Fukao H, Tomioka Y, Ueshima S, Watanuki M, Sakai M: Thrombolytic properties of staphylokinase. Blood 76: 925–929, 1990.
12. Lijnen HR, Van Hoef B, De Cock F, Okada K, Ueshima S, Matsuo O, Collen D: On the mechanism of fibrin-specific plasminogen activation by staphylokinase. J Biol Chem 266: 11826–11832, 1991.
13. Lijnen HR, Van Hoef B, Matsuo O, Collen D: On the molecular interactions between plasminogen-staphylokinase, $\alpha_2$-antiplasmin and fibrin. Biochim Biophys Acta 1118: 144–148, 1992.
14. Silence K, Collen D, Lijnen HR: Interaction between staphylokinase, plasmin(ogen) and $\alpha_2$-antiplasmin. Recycling of staphylokinase after neutralization of the plasmin-staphylokinase complex by $\alpha_2$-antiplasmin. J Biol Chem 268: 9811–9816, 1993.
15.Silence K, Collen D, Lijnen HR: Regulation by $\alpha_2$-antiplasmin and fibrin of the activation of plasminogen with recombinant staphylokinase in plasma. Blood 82: 1175–1183, 1993.
16. Sakharov DV, Lijnen HR, Rijken DC. Interactions between staphylokinase, plasmin(ogen), and fibrin. J Biol Chem 271: 27912–27918, 1996.
17. Schlott B, Gührs KH, Hartmann M, Röcker A, Collen D. Staphylokinase requires $NH_2$-terminal proteolysis for plasminogen activation. J Biol Chem (in press).
18. Collen D, De Cock F, Vanlinthout I, Declerck PJ, Lijnen HR, Stassen JM. Comparative thrombolytic and immunogenic properties of staphylokinase and streptokinase. Fibrinolysis 6: 232–242, 1992.
19. Collen D, De Cock F, Stassen JM. Comparative immunogenicity and thrombolytic properties toward arterial and venous thrombi of streptokinase and recombinant staphylokinase in baboons. Circulation 87: 996–1006, 1993.
20. White H: Thrombolytic treatment for recurrent myocardial infarction. Br Med J 302: 429–430, 1991.
21. Gase A, Hartmann M, Gührs KH, Röcker A, Collen D, Behnke D, Schlott B: Functional significance of $NH_2$- and COOH-terminal regions of staphylokinase in plasminogen activation. Thromb Haemost 76: 755–760, 1996.
22. EP 95200023.0 (Jan. 6, 1995) and U.S. Ser. No. 08/499,092 (Jul. 6, 1995).
23. Schlott B, Hartmann M, Gührs KH, Birch-Hirschfeid E, Pohl HD, Vanderschueren S, Van de Werf F, Michoel A, Collen D, Behnke D: High yield production and purification of recombinant staphylokinase for thrombolytic therapy. Bio/technology 12: 185–189, 1994.
24. Horton RM, Hunt HD, Ho SN, Pullen JK, Pease LR. Engineering hybrid genes without the use of restriction enzymes: gene splicing by overlap extension. Gene 77: 61–68, 1989.
25. BIAcore system manual, 5-2, Pharmacia Biosensor AB, Uppsala, Sweden.
26. Karlsson R, Michaelsson A, Mattsson L: Kinetic analysis of monoclonal antibody-antigen interactions with a new biosensor based analytical system. J Immunol Methods 145: 229–240, 1991.
27. Sambrook J, Fritsch EF, Maniatis T: Molecular cloning: a laboratory mannual. 2nd Ed. Cold Spring Harbor, N.Y. Cold Spring Harbor Laboratory Press, 1989.
28. Tartof KD, Hobbs CA: Improved media for growing plasmid and cosmid clones. Bethesda Res Lab Focus 9: 12, 1987
29. Bradford MM: A rapid and sensitive method for the quantitation of microgram quantities of protein utilizing the principle of protein-dye binding. Anal Biochem 72: 248, 1976.
30. Deutsch DG, Mertz ET: Plasminogen: purification from human plasma by affinity chromatography. Science 170: 1095–1096, 1970.
31. Vanderschueren S, Stockx L, Wilms G, Lacroix H, Verhaeghe R, Vermylen J, Collen D:
Thrombolytic therapy of peripheral arterial occlusion with recombinant staphylokinase. Circulation 92: 2050–2057, 1995.

TABLE 1

Apparent equilibrium association constants ($K_A \times 10^7$ $M^{-1}$) for the binding of wild-type SakSTAR and of SakSTAR variants obtained by "alanine-to-wild-type" reversal of "charged-cluster-to-alanine" mutants to be insolubilized murine monoclonal antibodies (MAbs).

| | | Spec. Act. | murine MAbs | | | | | | | | | |
|---|---|---|---|---|---|---|---|---|---|---|---|---|
| | | (× $10^3$ | Epitope I | | | | | Epitope II | | | | |
| Compound | Substituted amino acid | HU/mg) | 17G11 | 26A2 | 30A2 | 2B12 | 3G10 | 18F12 | 14H5 | 28H4 | 32B2 | 7F10 |
| SakSTAR | | 130 | 22 | 13 | 2.9 | 7.8 | 11 | 38 | 7.4 | 19 | 7.7 | 2.4 |
| SakSTAR($KE_{38}$) | K35A, E38A | 97 | 15 | 22 | 4.2 | 11 | 7.9 | 110 | 10 | 15 | 12 | 2.2 |
| SakSTAR($K_{74}ER$) | K74A, E75A, R77A | 110 | 11 | <.01 | <0.1 | <0.1 | <0.1 | 150 | 17 | 28 | 14 | 3.3 |
| SakSTAR(KEKER) | K35A, E38A, K74A, E75A, R77A | 50 | 11 | <0.1 | <0.1 | <0.1 | <0.1 | 110 | 36 | 26 | 15 | 2.0 |
| SakSTAR(EKER) | E38A, K74A, E75A, R77A | 43 | 11 | <0.1 | <0.2 | <0.1 | <0.1 | 140 | 39 | 26 | 15 | 2.1 |
| SakSTAR(KKER) | K35A, K74A, E75A, R77A | 56 | 9.2 | <0.1 | 0.15 | <0.1 | <0.1 | 52 | 14 | 29 | 8.8 | 2.3 |
| SakSTAR(KEER) | K35A, E38A, E75A, R77A | 44 | 11 | 0.3 | 0.1 | 0.2 | <0.1 | 75 | 9.8 | 12 | 7.3 | 1.6 |
| SakSTAR(KEKR) | K35A, E38A, K74A, R77A | 41 | 8.8 | 2.9 | <0.1 | 2.0 | 0.33 | 110 | 29 | 31 | 10 | 2.0 |
| SakSTAR($KEKE_{75}$) | K3SA, E38A, K74A, E75A | 19 | 13 | <0.1 | 0.1 | <0.1 | <0.1 | 180 | 41 | 37 | 15 | 1.6 |
| SakSTAR(EER) | E38A, E75A, R77A | 88 | 11 | 0.6 | 0.15 | 0.4 | 0.3 | 79 | 12 | 15 | 10 | 2.0 |
| SakSTAR($EE_{75}$) | E38A, E75A | 66 | 16 | 0.3 | <0.1 | <0.1 | 0.9 | 56 | 11 | 13 | 8.9 | 2.0 |
| SakSTAR($K_{35}E_{75}R$) | K3SA, E75A, R77A | 68 | 9.2 | <0.1 | <0.1 | <0.1 | <0.1 | 60 | 7.0 | 13 | 11 | 3.3 |
| SakSTAR($K_{35}E_{75}$) | K3SA, E75A | 150 | 17 | 0.12 | <0.1 | 0.16 | 0.14 | 40 | 7.2 | 13 | 9.2 | 4.2 |

TABLE 1-continued

Apparent equilibrium association constants ($K_A \times 10^7\ M^{-1}$) for the binding of wild-type SakSTAR and of SakSTAR variants obtained by "alanine-to-wild-type" reversal of "charged-cluster-to-alanine" mutants to be insolubilized murine monoclonal antibodies (MAbs).

| | | | | | | | | | | | | |
|---|---|---|---|---|---|---|---|---|---|---|---|---|
| SakSTAR($K_{74}$) | K74A | 100 | 12 | 7.6 | 0.17 | 4.4 | 2.1 | 55 | 15 | 33 | 14 | 3.6 |
| SakSTAR($E_{75}$) | E75A | 140 | 13 | 1.2 | <0.1 | <0.1 | <0.1 | 46 | 8.5 | 14 | 12 | 3.4 |
| SakSTAR($K_{74}$ERED) | K74A, E75A, R77A, E80A, D82A | 50 | 14 | <0.1 | <0.1 | <0.1 | <0.1 | 180 | 19 | 33 | 19 | 3.7 |
| SakSTAR($E_{80}$D) | E80A, D82A | 130 | 7.3 | 12 | 2.1 | 6.5 | 5.9 | 79 | 6.1 | 8.4 | 7.8 | 1.9 |
| SakSTAR($E_{80}$) | E80A | 160 | 13 | 13 | 3.3 | 7.9 | 10 | 35 | 7.4 | 17 | 8.6 | 2.1 |
| SakSTAR(D) | D82A | 160 | 17 | 12 | 4.8 | 7.3 | 11 | 31 | 7.8 | 17 | 12 | 2.7 |
| SakSTAR($E_{75}$D) | E75A, D82A | 170 | 20 | 15 | 3.1 | 6.6 | 7.2 | 69 | 8.1 | 15 | 14 | 4.9 |

| Compound | Substituted amino acids | Spec. Act. (× $10^3$ HU/mg) | murine MAbs Epitope III 7H11 | 25E1 | 40C8 | 24C4 | 1A10 |
|---|---|---|---|---|---|---|---|
| SakSTAR | | 130 | 4.0 | 14 | 5.4 | 2.9 | 0.6 |
| SakSTAR($KE_{38}$) | K35A, E38A | 97 | <0.1 | <0.1 | <0.1 | 1.0 | 1.0 |
| SakSTAR($K_{74}$ER) | K74A, E75A, R77A | 110 | 2.4 | 11 | 4.0 | 2.1 | 0.9 |
| SakSTAR(KEKER) | K35A, E38A, K74A, E75A, R77A | 50 | <0.1 | <0.1 | <0.1 | 1.5 | 1.2 |
| SakSTAR(EKER) | E38A, K74A, E75A, R77A | 43 | <0.1 | 3.2 | 3.7 | 1.6 | 1.1 |
| SakSTAR(KKER) | K35A, K74A, E75A, R77A | 56 | <0.1 | 1.8 | <0.1 | 1.8 | 0.8 |
| SakSTAR(KEER) | K35A, E38A, E75A, R77A | 44 | <0.1 | <0.1 | <0.1 | 0.53 | 0.64 |
| SakSTAR(KEKR) | K35A, E38A, K74A, R77A | 41 | <0.1 | <0.1 | <0.1 | 0.63 | 0.74 |
| SakSTAR($KEKE_{75}$) | K3SA, E38A, K74A, E75A | 19 | <0.1 | <0.1 | <0.1 | 1.2 | 0.45 |
| SakSTAR(EER) | E38A, E75A, R77A | 88 | <0.1 | 2.6 | 4.7 | 1.1 | 0.81 |
| SakSTAR($EE_{75}$) | E38A, E75A | 66 | <0.1 | 20 | 4.8 | 1.3 | 1.6 |
| SakSTAR($K_{35}E_{75}$R) | K3SA, E75A, R77A | 68 | <0.1 | 1.5 | <0.1 | 0.8 | 1.1 |
| SakSTAR($K_{35}E_{75}$) | K3SA, E75A | 150 | <0.1 | 1.8 | <0.1 | 1.4 | 1.5 |
| SakSTAR($K_{74}$) | K74A | 100 | 2.9 | 14 | 4.9 | 3.4 | 1.2 |
| SakSTAR($E_{75}$) | E75A | 140 | 4.5 | 18 | 5.0 | 1.2 | 2.1 |
| SakSTAR($K_{74}$ERED) | K74A, E75A, R77A, E80A, D82A | 50 | <0.1 | <0.1 | <0.1 | <0.1 | 1.2 |
| SakSTAR($E_{80}$D) | E80A, D82A | 130 | <0.1 | <0.1 | <0.1 | <0.1 | 0.44 |
| SakSTAR($E_{80}$) | E80A | 160 | <0.1 | 16 | 3.6 | <0.1 | 1.7 |
| SakSTAR(D) | D82A | 160 | <0.1 | 0.18 | <0.1 | <0.1 | 2.3 |
| SakSTAR($E_{75}$D) | E75A, D82A | 170 | 0.17 | 0.7 | 0.5 | 0.1 | 1.4 |

Apparent association constants ≧ 10-fold lower than those of wild-type SakSTAR are represented in bold type; ≧65.000 HU/mg represented in bold type.
M3, M8, M9, M3.8, M8.9 denotes SakSTAR variants previously stsudied (22), but in reverse order (binding of soluble Mab to insolubilized variant.

TABLE 2

Absorption with wild-type SakSTAR variants obtained by "alanine-to-wild-type" reversal of "charged-cluster-to-alanine" mutants, elicited with wild-type SakSTAR in patients with acute myocardial infarction.

| Compound | Substituted amino acids | Spec. Act. (× $10^3$ HU/mg) | Human plasma Pool | Subpool B | Subpool C |
|---|---|---|---|---|---|
| SakSTAR | | 130 | 95 | 95 | 95 |
| SakSTAR($KE_{38}$) | K35A, E38A | 97 | 93 | 91 | 94 |
| SakSTAR($K_{74}$ER) | K74A, E75A, R77A | 110 | 55 | 43 | 95 |
| SakSTAR(KEKER) | K35A, E38A, K74A, E75A, R77A | 50 | 52 | 41 | 92 |
| SakSTAR(EKER) | E38A, K74A, E75A, R77A | 43 | 50 | 44 | 95 |
| SakSTAR(KKER) | K35A, K74A, E75A, R77A | 56 | 46 | 43 | 95 |
| SakSTAR(KEER) | K35A, E38A, E75A, R77A | 44 | 92 | 87 | 94 |
| SakSTAR(KEKR) | K35A, E38A, K74A, R77A | 41 | 56 | 50 | 93 |
| SakSTAR($KEKE_{75}$) | K35A, E38A, K74A, E75A | 19 | 48 | 41 | 92 |
| SakSTAR(EER) | E38A, E75A, R77A | 88 | 95 | 88 | 95 |
| SakSTAR($EE_{75}$) | E38A, E7SA | 66 | 91 | 90 | 95 |
| SakSTAR($K_{35}E_{75}$R) | K35A, E75A, R77A | 68 | 88 | 89 | 95 |
| SakSTAR($K_{35}E_{75}$) | K35A, E75A | 150 | 94 | 93 | 95 |
| SakSTAR($K_{74}$) | K74A | 100 | 59 | 45 | 95 |
| SakSTAR($E_{75}$) | E75A | 140 | 95 | 93 | 95 |
| SakSTAR($K_{74}$ERED) | K74A, E75A, R77A, E80A, D82A | 50 | 49 | 29 | 89 |
| SakSTAR($E_{80}$D) | E80A, D82A | 130 | 89 | 83 | 92 |
| SakSTAR($E_{80}$) | E80A | 160 | 94 | 93 | 95 |
| SakSTAR(D) | D82A | 160 | 95 | 93 | 95 |
| SakSTAR($E_{75}$D) | E75A, D82A | 170 | 95 | 95 | 95 |

≦80% absorption represented in bold type; >65.000 HU/mg represented in bold type.
The data represent percent ot antibodies absorbed by compound, determined from the residual binding to insolubilized SakSTAR.

TABLE 3

Apparent equilibrium association constants ($K_A \times 10^7$ $M^{-}$) for the binding of wild-type SakSTAR and of site-specific SakSTAR variants to insolubilized murine monoclonal antibodies (Mabs)

| | | Spec. Act. | Epitope I | | | | | Epitope II | | | | | Epitope III | | | | |
|---|---|---|---|---|---|---|---|---|---|---|---|---|---|---|---|---|---|
| Compound | Substituted amino acids | ($\times 10^3$ HU/mg) | 17G11 | 26A2 | 30A2 | sB12 | 3G10 | 18F12 | 14H5 | 28H4 | 32B2 | 7F10 | 7H11 | 25E1 | 40C8 | 24C4 | 1A10 |
| SakSTAR | | 130 | 22 | 13 | 2.9 | 7.8 | 11 | 38 | 7.4 | 19 | 7.7 | 2.4 | 4.0 | 14 | 5.4 | 2.9 | 0.6 |
| SakSTAR.M27 | Y17A, FI8A | 30 | 13 | 22 | 3.3 | 10 | 9.5 | 21 | 4.6 | 6.7 | 12 | 2.5 | 1.2 | 18 | 6.5 | 3.4 | <0.1 |
| SakSTAR.M2223 | F47A | <5 | <0.1 | 4 | 1 | 3.9 | 3.4 | 5.7 | 2.7 | 2.8 | 8.5 | 1.7 | 0.9 | 8.8 | 3 | 3 | 0.93 |
| SakSTAR.M5051 | F76A | 90 | 20 | 9.6 | 1 | 2.7 | 3.9 | 13 | 6.2 | 20 | 15 | 1.7 | 0.32 | 5.9 | 2.1 | 1.2 | 1 |
| SakSTAR.M46 | F104A | 55 | 5.8 | 19 | 4.8 | 14 | 27 | 7.3 | 5 | 14 | 4.8 | <0.1 | 0.4 | 7.6 | 3.4 | 1.1 | 1.3 |
| SakSTAR.M48 | F111A | 49 | 3.7 | 16 | 3.8 | 13 | 22 | 21 | 8.4 | 12 | 3.1 | 0.8 | | | | | |
| SakSTAR.M2426 | F125A | <10 | 2.8 | 18 | 4.7 | 11 | 18 | 17 | 3.2 | 6 | 1.9 | <0.1 | 0.3 | 5.3 | 2.1 | 0.9 | 1.6 |
| SakSTAR.M44 | Y9A | 78 | 22 | 49 | 6.6 | 2.3 | 16 | 44 | 8.4 | 20 | 14 | 2.6 | 2.4 | 16 | 9.6 | 1.1 | 0.46 |
| SakSTAR.M3839 | Y24A | 40 | 17 | 33 | 4.3 | 13 | 11 | 33 | 4.3 | 7 | 12 | 4 | 0.36 | 14 | 6.8 | 4.8 | <0.1 |
| SakSTAR.M2021 | H43A, Y44A | <5 | 10 | 22 | 3.7 | 17 | 15 | <0.1 | <0.1 | <0.1 | 1.4 | 3 | 2.3 | 11 | 5.2 | 2.1 | 0.13 |
| SakSTAR.M99100 | Y62V | 2 | 3 | 2.2 | 1.8 | 3.5 | 3 | 21 | 5.7 | 6.6 | 18 | 3.5 | 1.9 | 8.1 | 4.5 | 5.8 | 0.89 |
| SakSTAR.M8384 | Y63A | <5 | <0.1 | 18 | 3.7 | 9.6 | 13 | 17 | 5.3 | 3.3 | 15 | 1.1 | 2.2 | 5.3 | 4.3 | 1 | 3.7 |
| SakSTAR.M2528 | Y62A, Y63A | <5 | <0.1 | 4.3 | 0.3 | 2.1 | 1.9 | 11 | 2.2 | 3.1 | 8.4 | 1.7 | 0.6 | 9.2 | 3.6 | 3.8 | 0.7 |
| SakSTAR.M3031 | Y73A | <5 | 9.5 | <0.1 | <0.1 | <0.1 | 4.8 | 33 | 7.3 | 11 | 8.9 | 2 | 0.5 | 9 | 2.5 | 1.4 | 0.75 |
| SakSTAR.M145146a | Y73F | 31 | 7.9 | 12 | 1.3 | 2.1 | 8 | 24 | 15 | 19 | 15 | 2.6 | 1.6 | 6.2 | 3.5 | 7.2 | 1.4 |
| SakSTAR.M145146b | Y73L | 1.8 | 11 | <0.1 | <0.1 | <0.1 | <0.1 | 84 | 19 | 26 | 53 | 3.4 | 4.2 | 7.1 | 4.2 | 3.4 | 0.95 |
| SakSTAR.M169170 | Y73H | <2 | 7.3 | 1.5 | <0.1 | <0.1 | 1.4 | 20 | 7.5 | 17 | 42 | 4.3 | 3.5 | 6.8 | 5.9 | 9.7 | 1.3 |
| SakSTAR.M171172 | Y73W | 27 | 4.8 | 9 | 4.6 | 4.6 | 11 | 8.4 | 4.5 | 11.2 | 8 | 2.7 | 2.9 | 5 | 3 | 3.8 | 1.3 |
| SakSTAR.M145145c | Y73S | <5 | 7 | 3.6 | 0.59 | 0.6 | 3 | 21 | 8.3 | 14 | 21 | 3.2 | 2.2 | 6.7 | 1.3 | 1.3 | 0.67 |
| SakSTAR.M165166 | Y73F, F76Y | 10 | 8.4 | 17 | 4.5 | 2.6 | 10 | 33 | 18 | 34 | 21 | 4.5 | 5.2 | 8.7 | 8.1 | 1.3 | 1.9 |
| SakSTAR.M7980 | Y73A, K74A | <5 | 18 | <0.1 | <0.1 | <0.1 | <0.1 | 19 | 6.7 | 23 | 9.9 | 3.2 | 2.7 | 13 | 4 | 1.6 | 1.1 |
| SakSTAR.M8990 | Y73F, K74A | 5.6 | 17 | 6.7 | <0.1 | 2.1 | <0.1 | 42 | 19 | 21 | 20 | 4.9 | 1.9 | 2.8 | 6.6 | 2.1 | 0.84 |
| SakSTAR.M53 | Y91A | 53 | 6 | 16 | 3 | 7 | 13 | 28 | 8.2 | 16 | 0.6 | 2.1 | 1.4 | 3.7 | 1.6 | 1.6 | 0.2 |
| SskSTAR.M54 | Y92A | 118 | 16 | 23 | 4.1 | 13 | 12 | 29 | 7.3 | 18 | <0.1 | 1.7 | 4.4 | 10 | 3.9 | 5.9 | 1.1 |
| SakSTAR.M5960 | H43A | 69 | 15 | 28 | 9.7 | 18 | 7.6 | <0.1 | <0.1 | <0.1 | 9.1 | 1.5 | 2 | 23 | 7.8 | 7.2 | 1.6 |
| SakSTAR.M6162 | H43R | 120 | 15 | 11 | 2.7 | 7.6 | 11 | <0.1 | <0.1 | <0.1 | 13 | 6.4 | 0.7 | 18 | 6.7 | 57 | 1.4 |
| SakSTAR.M6364 | I49A | 43 | 2.7 | 27 | 7.8 | 23 | 22 | 35 | 4.4 | 11 | 6.2 | 1.1 | 2 | 5.7 | 2 | 1.7 | 0.6 |
| SakSTAR.M6566 | I60A | 96 | 12 | 20 | 2.9 | 11 | 13 | 27 | 6.4 | 25 | 2.7 | 1.5 | 0.7 | 5.8 | 2.9 | 1.7 | 1 |
| SakSTAR.M55 | I87A | 98 | 6.7 | 23 | 2.8 | 8.6 | 9.1 | 10 | 3.6 | 11 | 7.4 | 2.7 | 1.1 | 7.8 | 3.4 | 4.5 | 1 |
| SakSTAR.M67 | I106A | 93 | 2.3 | 13 | 3 | 7.4 | 6.7 | 5.5 | 5.2 | 17 | 11 | 1.4 | 1.8 | 3.1 | 1.8 | 1.2 | 0.5 |
| SakSTAR.M56 | I120A | 75 | 23 | 26 | 5.1 | 17 | 16 | 30 | 9.8 | 25 | 9 | 6.9 | 3 | 15 | 5.1 | 5.2 | 1 |
| SakSTAR.M57 | I128A | 20 | 16 | 25 | 48 | 15 | 14 | 38 | 2.6 | 4.3 | 8.2 | 2.9 | 2.5 | 2 | 4.2 | 6.7 | 0.9 |
| SakSTAR.M58 | 1133A | 99 | 9.4 | 15 | 1.9 | 7.8 | 7.8 | 24 | 6 | 9.1 | 8.6 | 1.4 | 0.56 | 6.4 | 1.6 | 1.6 | 0.9 |
| SakSTAR.M130131 | V29A, N28A | 45 | 18 | 30 | 2.5 | 20 | 18 | 20 | 14 | 20 | 24 | 2.7 | 3.3 | 20 | 1.1 | 5 | 2 |
| SakSTAR.M9596 | V32A | 45 | 10 | 9.6 | 2.4 | 6.2 | 7.8 | 56 | 17 | 12 | 14 | 1.4 | <0.1 | <0.1 | <0.1 | <0.1 | 2.2 |
| SakSTAR.M7576 | V45A | <5 | 16 | 5.6 | 1.4 | 4.8 | 6.3 | 2.2 | 0.23 | 1.7 | 32 | 2.6 | 2.1 | 8.3 | 1.1 | 2.8 | 1.6 |
| SakSTAR.M9798 | V64A | 48 | 14 | 16 | 2.9 | 6.3 | 7.8 | 15 | 15 | 21 | 21 | 2.6 | 1.6 | 7.6 | 5.6 | 2.8 | 0.7 |
| SakSTAR.M120121 | V78A, V79A | 68 | 12 | 23 | 4 | 10 | 17 | 21 | 18 | 34 | 28 | 2.3 | 1.6 | 4.7 | <0.1 | 0.5 | 1.7 |
| SakSTAR.M140141 | V112A, V113A | 123 | 4.2 | 16 | 3.9 | 10 | 12 | 34 | 5.8 | 13 | 8 | 0.3 | 1.5 | 4.3 | 2.3 | 3 | 0.8 |
| SakSTAR.M7374 | L39A, L40A | <5 | 14 | 15 | 3.1 | 5.1 | 8 | 27 | 16 | 6.3 | 12 | 2.7 | 1.2 | 5.4 | 3.2 | 2.1 | 0.9 |
| SakSTAR.M9192 | L68A | 93 | 14 | 22 | 3.5 | 8.5 | 9.3 | 29 | 8.7 | 16 | 15 | 4 | 2.1 | 5.3 | 3.6 | 4.1 | <0.1 |
| SakSTAR.M124125 | L81A | 28 | 12 | 33 | 1.6 | 40 | 11 | 52 | 11 | 17 | 17 | 3.9 | 1.4 | 5.2 | 7.1 | 46 | 1.5 |
| SakSTAR.M128129 | L116A, 5117A | 4.8 | 4.4 | 35 | 3.6 | 33 | 42 | 156 | 29 | 218 | <0.1 | <0.1 | 0.48 | 4.1 | 4.9 | 35 | 1.6 |
| SakSTAR.M127 | L127A | 54 | 8.9 | 6.7 | 1.8 | 5 | 6.6 | 25 | 4.9 | 14 | 8.4 | 1.5 | 0.9 | 1.9 | 0.9 | 2.5 | 1.8 |

TABLE 3-continued

Apparent equilibrium association constants ($K_A \times 10^7\ M^-$) for the binding of wild-type SakSTAR and of site-specific SakSTAR variants to insolubilized murine monoclonal antibodies (Mabs)

| Compound | Substituted amino acids | Spec. Act. ($\times 10^3$ HU/mg) | Epitope I 17G11 | 26A2 | 30A2 | sB12 | 3G10 | Epitope II 18F12 | 14H5 | 28H4 | 32B2 | 7F10 | Epitope III 7H11 | 25E1 | 40C8 | 24C4 | 1A10 |
|---|---|---|---|---|---|---|---|---|---|---|---|---|---|---|---|---|---|
| SakSTAR.M7172 | S41A, P42A | 48 | 10 | 25 | 4.1 | 13 | 12 | 1i | 3 | 1.9 | 27 | 2.7 | 3.2 | 15 | 4.8 | 36 | 1.1 |
| SakSTAR.M8182 | S34A | 106 | 17 | 24 | 46 | 9.5 | 11 | 28 | 11 | 22 | 15 | 2.9 | 3.1 | 8.8 | 3.8 | 2 | 0.17 |
| SakSTAR.M9394 | S84A | 08 | 15 | 19 | 4.9 | 12 | 17 | 47 | 12 | 22 | 35 | 2 | 0.3 | 1.9 | 1.4 | 5.5 | 1.5 |
| SakSTAR.M7778 | N37A | 110 | 5.6 | 31 | 3 | 10 | 11 | 20 | 4.1 | 14 | 10 | 2.9 | 1.4 | 5.3 | 3.5 | 3.6 | 0.8 |
| SakSTAR.M133134 | N95A | 263/445 | 10 | 18 | 4 | 10 | 11 | 50 | 13 | 14 | 4.9 | 2.3 | 3.7 | 7.3 | 4.7 | 2.9 | 0.8 |
| SakSTAR.M137 | N126V | 51 | 7.6 | 13 | 2 | 12 | 13 | 30 | 58 | 290 | 9.8 | 2.5 | 1.8 | 8 | 4.2 | 6.5 | 0.7 |
| SakSTAR.M159160 | M26L | 38 | 5.3 | 14 | 2.2 | 6.6 | 6.5 | 48 | 3.7 | 2.4 | 3.7 | 2.4 | 2 | 4.1 | 2.2 | 2 | 0.3 |
| SakSTAR.M161162 | M26V | <2 | 6.3 | 14 | 3.8 | 9.1 | 12 | 26 | 2 | 1.5 | 4.3 | 1.1 | 1.8 | 4.9 | 2.2 | 2.5 | 0.46 |
| SakSTAR.M105106 | G36K | 88 | 9.9 | 23 | 3.1 | 8.3 | 9.8 | 21 | 3.9 | 13 | 15 | 3 | <0.1 | <0.1 | <0.1 | 2.6 | 1.2 |
| SakSTAR.M103104 | G36R | 102 | 11 | 24 | 3.3 | 10 | 10 | 27 | 4.6 | 14 | 20 | 3A | <0.1 | <0.1 | <0.1 | 3.1 | 1.2 |
| SakSTAR.M103104+ | G36R, K74A | 65 | 19 | 7 | 0.22 | 4.3 | 2 | 53 | 27 | 28 | 19 | 4.4 | <0.1 | <0.1 | <0.1 | 1.2 | 1 |
| SakSTAR.M3637 | E19A, P20A | 9 | 11 | 19 | 3.3 | 9.2 | 12 | 15 | 6.1 | 11 | 16 | 1 | 1.1 | 15 | 5.1 | 3.3 | <0.1 |
| SakSTAR.M8788 | P23A | 67 | 14 | 31 | 4.4 | 14 | 22 | 41 | 5.3 | 37 | 13 | 10 | 4 | 11 | 7.6 | 3.1 | 1.9 |
| SakSTAR.M8586 | W66A | <5 | <0.1 | <0.1 | <0.1 | <0.1 | <0.1 | 15 | 4.4 | 5.7 | 23 | 3.3 | 2 | 10 | 1.4 | 1.8 | 0.83 |
| SakSTAR.M167168a | A725 | 190 | 4 | 3.8 | 2.4 | 1.3 | 1.8 | 30 | 5.6 | 7.4 | 1.7 | 1.7 | 1.7 | 5 | 2.2 | 5.5 | 0.4 |
| SakSTAR.M153154 | D13A | 46 | 2.4 | 6.1 | 2 | 3.7 | 3.4 | 11 | 1.9 | 4.5 | 4.4 | 8.7 | 1.5 | 2.4 | 1.1 | 3.6 | <0.1 |
| SakSTAR.M155156 | D14A | 30 | 5.1 | 13 | 4 | 6.6 | 3.1 | 38 | 7.7 | 12 | 15 | 2.2 | 2.7 | 6 | 3.2 | 5.6 | <0.1 |
| SakSTAR.M111112 | D69E | <5 | 14 | 5.7 | 1.2 | 2.6 | 2.2 | 23 | 4.3 | 15 | 18 | 4 | 1.5 | 11 | 6 | 4.1 | 1.1 |
| SakSTAR.M113114 | D69N | 6/(43) | 15 | 29 | 6.9 | 10 | 17 | 25 | 17 | 34 | 24 | 9.8 | 3.2 | 15 | 8.6 | 3.6 | 1 |
| SakSTAR.M149150 | E99A | 42 | 7.4 | 15 | 4 | 8.4 | 8.9 | 22 | 2.7 | 4.7 | <0.1 | <0.1 | 2.1 | 6.2 | 7.3 | 14 | 0.77 |
| SakSTAR.M109110a | K50A | 42 | <0.1 | 13 | 2.9 | 7.8 | 8.7 | 46 | 8.3 | 12 | 2.2 | 0.5 | 2.8 | 6.4 | 4 | 2.3 | 0.57 |
| SakSTAR.M151152a | K102A | 89 | 4.9 | 12 | 3.7 | 6.5 | 6.3 | 30 | 3.1 | 15 | 8.2 | 6.1 | 0.84 | 4.2 | 1.9 | 10 | 0.62 |

Apparent association constants ≧ 10-fold lower than those of wild-type SakSTAR are represented in bold type; ≧65.000 HU/mg represented in bold type.

TABLE 4

Absorptino with wild-type SakSTAR and with site-specific SakSTAR variants of antibodies elicited with wild-type SakSTAR in patients with acute myocardial infarction

| Compound | Substituted amino acids | Spec. Act. ($\times 10^3$ HU/mg) | Human plasma Pool | Subpool B | Subpool C |
|---|---|---|---|---|---|
| SakSTAR | | 130 | 95 | 95 | 95 |
| SakSTAR.M27 | Y17A, F18A | 30 | 95 | 95 | 95 |
| SakSTAR.M2223 | F47A | <5 | 90 | 82 | 97 |
| SakSTAR.M5051 | FY6A | 90 | 94 | 92 | 95 |
| SakSTAR.M46 | F104A | 55 | 95 | 93 | 95 |
| SakSTAR.M48 | F111A | 49 | 95 | 95 | 95 |
| SakSTAR.M2426 | F125A | <10 | 93 | 90 | 95 |
| SakSTAR.M44 | Y9A | 78 | 96 | 95 | 95 |
| SakSTAR.M3839 | Y24A | 40 | 95 | 95 | 95 |
| SakSTAR.M2021 | H43A, Y44A | <5 | 95 | 95 | 95 |
| SakSTAR.M99100 | Y62V | 2 | 92 | 86 | 95 |
| SakSTAR.M8384 | Y63A | <5 | 89 | 82 | 95 |
| SakSTAR.M2528 | Y62A, Y63A | <5 | 89 | 83 | 95 |
| SakSTAR.M3031 | Y73A | <5 | 63 | 44 | 93 |
| SakSTAR.M145146a | Y73F | 31 | 93 | 95 | 95 |
| SakSTAR.M145146b | Y73L | 1.8 | 81 | 60 | 94 |
| SakSTAR.M169170 | Y73H | <2 | 76 | 65 | 95 |
| SakSTAR.M171172 | Y73W | 27 | 73 | 53 | 93 |
| SakSTAR.M145145c | Y735 | <5 | 66 | 69 | 95 |
| SakSTAR.M165166 | Y73F, F76Y | 10 | 94 | 85 | 95 |
| SakSTAR.M7980 | Y73A, K74A | <5 | 47 | 28 | 87 |
| SakSTAR.M8990 | Y73F, K74A | 5.6 | 51 | 34 | 90 |
| SakSTAR.M53 | Y91A | 5.3 | 95 | 95 | 95 |
| SakSTAR.M54 | Y92A | 118 | 94 | 95 | 95 |
| SakSTAR.M5960 | H43A | 69 | 95 | 95 | 95 |
| SakSTAR.M6162 | H43R | 120 | 95 | 95 | 95 |
| SakSTAR.M6364 | I49A | 43 | 95 | 95 | 95 |
| SakSTAR.M6566 | I60A | 96 | 95 | 95 | 95 |
| SakSTAR.M55 | I87A | 98 | 95 | 95 | 95 |
| SakSTAR.M67 | I106A | 93 | 95 | 95 | 95 |
| SakSTAR.M56 | I120A | 75 | 93 | 95 | 95 |
| SakSTAR.M57 | I128A | 20 | 95 | 93 | 95 |
| SakSTAR.M58 | I133A | 99 | 95 | 95 | 95 |
| SakSTAR.M130131 | V29A, N28A | 45 | 93 | 95 | 95 |
| SakSTAR.M9596 | V32A | 45 | 90 | 93 | 95 |
| SakSTAR.M7576 | V45A | <5 | 91 | 92 | 95 |
| SakSTAR.M9798 | V64A | 48 | 94 | 92 | 95 |
| SakSTAR.M120121 | V78A, V79A | 68 | 93 | 93 | 95 |
| SakSTAR.M140141 | V112A, V113A | 123 | 95 | 95 | 95 |
| SakSTAR.M7374 | L39A, L40A | <5 | 93 | 93 | 95 |
| SakSTAR.M9192 | L68A | 93 | 92 | 92 | 95 |
| SakSTAR.M124125 | L81A | 28 | 88 | 95 | 95 |
| SakSTAR.M128129 | L116A, S117A | 4.8 | 94 | 95 | 95 |
| SakSTAR.M127 | L127A | 54 | 93 | 94 | 95 |
| SakSTAR.M7172 | S41A, P42A | 48 | 95 | 95 | 95 |
| SakSTAR.M8182 | S34A | 106 | 95 | 95 | 93 |
| SakSTAR.M9394 | S84A | 88 | 95 | 94 | 95 |
| SakSTAR.M7778 | N37A | 110 | 95 | 95 | 95 |
| SakSTAR.M133134 | N95A | 263/445 | 95 | 95 | 95 |
| SakSTAR.M137 | N126V | 51 | 95 | 95 | 95 |
| SakSTAR.M159160 | M26L | 38 | 95 | 95 | 95 |
| SakSTAR.M161162 | M26V | <2 | 95 | 94 | 95 |
| SakSTAR.M105016 | G36K | 88 | 88 | 80 | 69 |
| SakSTAR.M103014 | G36R | 102 | 89 | 81 | 70 |
| SakSTAR.M103104+ | G36R, K74A | 65 | 48 | 33 | 58 |
| SakSTAR.M3637 | E19A, P20A | 9 | 93 | 93 | 95 |
| SakSTAR.M8788 | P23A | 67 | 91 | 95 | 95 |
| SakSTAR.M8586 | W66A | <5 | 85 | 78 | 92 |
| SakSTAR.M167168a | A72S | 190 | 95 | 93 | 95 |
| SakSTAR.M153154 | D13A | 46 | 95 | 94 | 95 |
| SakSTAR.M155156 | D14A | 30 | 95 | 94 | 95 |
| SakSTAR.M111112 | D69E | <5 | 86 | 78 | 95 |
| SakSTAR.M113114 | D69N | 6/(43) | 84 | 81 | 89 |
| SakSTAR.M149150 | E99A | 42 | 92 | 91 | 92 |
| SakSTAR.M109110a | K50A | 42 | 95 | 94 | 95 |
| SakSTAR.M151152a | K102A | 89 | 95 | 93 | 95 |

≦80% absorption represented in bold type; >65.000 HU/mg represented in bold type.
The data represent percent of antibodies absorbed by compound, determined from the residual binding to insolubilized SakSTAR.

TABLE 5

Selected variants with ≧50% residual activity, ≧10 fold reduced binding of murine MAb, and ≦80% absorption of human antibodies eleicited by treatment with wild-type SakSTAR.

| Substituted amino acids | Spec. Act. (× $10^3$ HU/mg) | murine MAbs: Epitope I: 17G11 | 26A2 | 30A2 | 2B12 | 3G10 | Epitope II: 18F12 | 14H5 | 28H4 | 32B2 | 7F10 | Epitope III: 7H11 | 25E1 | 40C8 | 24C4 | 1A10 |
|---|---|---|---|---|---|---|---|---|---|---|---|---|---|---|---|---|
| K74A, E75A, R77A | 110 | 11 | <.01 | <0.1 | <0.1 | <0.1 | 150 | 17 | 28 | 14 | 3.3 | 2.4 | 11 | 4.0 | 2.1 | 0.9 |
| K74A | 100 | 12 | 7.6 | 0.17 | 4.4 | 2.1 | 55 | 15 | 33 | 14 | 3.6 | 2.9 | 14 | 4.9 | 3.4 | 1.2 |
| G36K | 88 | 9.9 | 23 | 3.1 | 8.3 | 9.8 | 21 | 3.9 | 13 | 15 | 3 | <0.1 | <0.1 | <0.1 | 2.6 | 1.2 |
| G36R | 102 | 11 | 24 | 3.3 | 10 | 10 | 27 | 4.6 | 14 | 20 | 3.4 | <0.1 | <0.1 | <0.1 | 3.1 | 1.2 |
| G36R, K74A | 65 | 19 | 7 | 0.22 | 4.3 | 2 | 53 | 27 | 28 | 19 | 4.4 | <0.1 | <0.1 | <0.1 | 1.2 | 1 |

| Substituted amino acids | Spec. Act. (× $10^3$ HU/mg) | Human plasma: Pool | Subpool B | Subpool C |
|---|---|---|---|---|
| K74A, E75A, R77A | 110 | 55 | 43 | 95 |
| K74A | 100 | 59 | 45 | 95 |
| G36K | 88 | 88 | 80 | 69 |
| G36R | 102 | 89 | 81 | 70 |
| G36R, K74A | 48 | 33 | 58 | |

TABLE 6

Characteristics of the patients with peripheral arterial occlusion treated with SakSTAR, SakSTAR($K_{74}$) or SakSTAR($K_{74}$ER)

| Compound Patient Id. | Gender | Age (yrs) | Clinical presentation | Risk factors Relevant history | Current Smoking | Locus of occlusion | Age of occluison (days) | Length of occlusion (cm) |
|---|---|---|---|---|---|---|---|---|
| SakSTAR | | | | | | | | |
| MEE | F | 67 | Ischemic rest pain | Hypertension, hyperlipidemia | + | Left SFA | 30 | 8 |
| FDR | M | 68 | Claudication | CAD, COPD, iliac stenting | + | Left IA (stent) | 14 | 18 |
| DAN | M | 73 | Claudication | CAD | − | Right SFA | 30 | 6 |
| BER | F | 63 | Ischemic rest pain | Hypertension, hyperlipidemia, AF and left FT graft | − | Left FT graft | 18 | 55 |
| DAM | F | 43 | Acute ischemia | Hypertension, claudication left arm | + | Left brachial and radial artery | 2 | 7 |
| TCR | M | 68 | Claudication | Hyperlipidemia, CABG, abdominal aortic aneurysm repair | − | Right SFA (popliteal aneurysm) | 50 | 12 |
| CLA | M | 74 | Acute ischemia | Hyperlipidemia, CAD, acute right SFA occlusion | + | Left PA | 1.5 | 20 |
| MAN | M | 65 | Acute ischemia | Diabetes, hypertension, left EIA stent | + | Left EIA (stent) | 4 | 20 |
| MAT | M | 64 | Subacute ischemia | Hypertension, CAD, aortobifemoral, left FP and right FT graft | − | Right FP graft | 3 | 45 |
| Mean ± SEM | | 65 ± 3.0 | | | | | 17 ± 5.6 | 21 ± 5.8 |
| SaKSTAR($K_{74}$) | | | | | | | | |
| LI | M | 70 | Subacute ischemia | Diabetes mellitus, CABG, right FF graft, left FP graft | − | Right FF graft | 10 | 48 |
| ENG | M | 50 | Claudication | Hypertension | + | Right SFA | 28 | 10 |
| CDX | F | 48 | Claudication | Hypertension, right PA graft | − | Right PA graft | 25 | 7 |
| MAN | F | 68 | Claudication | Hypertension, hyperilipidemia, CAD | − | Right SFA | ≧120 | 9 |
| VHE | M | 47 | Acute ischemia | Right IF graft | + | Right IF graft | 10 | 54 |
| MUL | F | 51 | Acute ischemia | Hypertension, right IF and FP graft | + | Right IF and FP graft | 1 | 63 |
| BUR | F | 67 | Ischemic rest pain | Diabetes mellitus, hypertension | − | Right TF trunc | 9.0 | 38 |
| NIJ | F | 60 | Ischemic rest | Hyperlipidemia, AF graft, | + | Left AF | 23 | 78 |

TABLE 6-continued

Characteristics of the patients with peripheral arterial occlusion treated with SakSTAR, SakSTAR($K_{74}$) or SakSTAR($K_{74}$ER)

| Compound Patient Id. | Gender | Age (yrs) | Clinical presentation | Risk factors Relevant history | Current Smoking | Locus of occlusion | Age of occluison (days) | Length of occlusion (cm) |
|---|---|---|---|---|---|---|---|---|
| | | | pain | carotid artery surgery | | graft | | |
| POE* | M | 49 | Subacute ischemia | Aortic coarctation repair, bilateral FP bypass | – | Right TF trunc | 2 | 30 |
| VBE | M | 39 | Subacute ischemia | Aneurysm right SC artery (thoracic outlet syndrome) | – | Right brachial artery (embolism) | 20 | 28 |
| SME | F | 50 | Subacute ischemia | Diabetes, hypertension, bilateral FT graft | – | TF trunc | 18 | 32 |
| WOL | M | 67 | Subacute ischemia | Diabetes, CAD, aortabilliac graft | + | Right PA | 4 | 25 |
| Mean ± SEM | | 56 ± 3.0 | | | | | 23 ± 9.2 | 35 ± 6.4 |
| SakSTAR($K_{74}$ER) | | | | | | | | |
| JAC | F | 65 | Acute ischemia | Hypertension, hyperlipidemia | – | Right brachial and ulnar artery | 0.3 | 5 |
| MAE | M | 74 | Ischemic rest pain | COPD, reimplantation superior mesenteric artery | + | Left SFA | 10 | 50 |
| CRA | F | 52 | Claudication | Mitral valve disease, ventricular and atrial fibrillation | – | Right IA and FA artery | 14 | 28 |
| VDB | M | 68 | Claudication | Hypertension, AF graft, carotid artery surgery | + | Left SFA | 90 | 12 |
| DUN | M | 71 | Subacute ischemia | DM, CAD | + | Left SFA | 14 | 6 |
| DEL | M | 59 | Acute ischemia | AF and right FT graft | + | Right FT graft | 3 | 42 |
| Mean ± SEM | | 65 ± 3.3 | | | | | 22 ± 14 | 24±7.8 |

AF aortofemoral; CABG: coronary artery bypass grafting; CAD, coronary artery disease; CIA: common iliac artery; COPD: chronic obstructive pulmonary disease; DM: diabetes mellitus; FF: femorofibular; FP: femoropopliteal; FT: femorotibial; IA: iliac artery; IF: iliofemoral; PA: popliteal artery; SFA: superficial femoral artery; TF: tibiofibular.
*Previous treatment with SakSTAR in 1994.

TABLE 7

Treatment and outcome in patients with peripheral arterial occlusion, treated with SakSTAR, SakSTAR(K74) or SakSTAR($K_{74}$ER)

| Compound Patient Id. | Recanalization by thrombolysis | Total dose of thrombolytic agent (mg) | Total duration of injfusion (hrs) | Additional therapy | Complications and remarks |
|---|---|---|---|---|---|
| SakSTAR | | | | | |
| MEE | complete | 7.0 | 5.0 | PTA | Puncture site bleeding, transfusion, reocclusion (day 3), femorotibial graft |
| FRO | complete | 6.5 | 4.5 | PTA + stent | Pyrexia (39° C.) |
| DAN | complete | 7.5 | 5.5 | PTA | — |
| EER | complete | 18 | 28 | PTA | Puncture site bleeding, transfusion |
| DAM | complete | 19 | 17 | PTA + stent | — |
| TOR | complete | 6.0 | 4.0 | PTA + femoropopliteal bypass graft | — |
| CLA | complete | 9.0 | 7.0 | — | — |
| MAN | complete | 6.5 | 4.5 | (amputation left digit V) | — |
| MAT | complete | 8.0 | 6.0 | (–) | — |
| Mean ± SEM | | 9.7 ± 1.7 | 9.1 ± 2.7 | | |
| SakSTAR($K_{74}$) | | | | | |
| UE | complete | 11 | 9.0 | PTA | — |
| ENG | complete | 12 | 10 | PTA | — |
| COX | partial | 15 | 15 | PTA | Reocclusion after PTA resistant to rt-PA, treated by surgical graft revision |
| MAN | complete | 9.0 | 7.0 | PTA | Puncture site hematoma, transfusion |
| VHE | complete | 18 | 16 | Surgical graft revision | — |

TABLE 7-continued

Treatment and outcome in patients with peripheral arterial occlusion, treated with SakSTAR, SakSTAR(K74) or SakSTAR($K_{74}$ER)

| Compound Patient Id. | Recanalization by thrombolysis | Total dose of thrombolytic agent (mg) | Total duration of injfusion (hrs) | Additional therapy | Complications and remarks |
|---|---|---|---|---|---|
| MUL | complete | 16 | 20 | PTA | — |
| BUR | partial | 18 | 21 | — | — |
| NIJ | complete | 15 | 21 | — | — |
| POE* | partial | 6.0 | 4.0 | rt-PA, surgical graft lengthening | Shivering and gastrointestinal disturbance; presumably of allergic origin, absence of recanalization despite switch to rt-PA |
| VBE | complete | 18 | 23 | Stent right SC artery, first rib resection | Retroperitoneal hematoma; hypovolemic shock; transfusion |
| SME | complete | 21 | 19 | None | None |
| WOL | complete | 16 | 22 | — | — |
| Mean ± SEM | | 15 ±1.2 | 16 ±1.9 | | |
| SakSTAR($K_{74}$ER) | | | | | |
| JAC | complete | 14 | 12 | — | Puncture site hematoma, transfusion |
| MAE | complete | 9.0 | 7.0 | PTA | — |
| CRA | complete | 25 | 23 | PTA + stent | |
| VDB | complete | 9.0 | 7.0 | PTA | — |
| DUN | complete | 9.0 | 7.0 | PTA | Reocclusion after 1 day; conservative management |
| DEL | complete | 9.0 | 7.0 | PTA | Reocclusion after 1 week treated with rt-PA |
| Mean ± SEM | | 13 ±2.6 | 11 ±2.6 | | |

PTA, percutaneous transluminal angioplasty
*Previous treatment with SakSTAR in 1994.

TABLE 8

Coagulation parameters before and after administration of SakSTAR, SakSTAR($K_{74}$) or SakSTAR($K_{74}$ER) in patients with peripheral arterial occlusion.

| Compound | Fibrinogen (g/l) | | Plasminogen (%) | | $\alpha_2$-antiplasmin (%) | | D-dimer (ng/ml) | | aPTT (s) | |
|---|---|---|---|---|---|---|---|---|---|---|
| Patient Id. | Before | After | Before | After | Before | After | Before | Peak | Before | After |
| SakSTAR | | | | | | | | | | |
| MEE | 2.4 | 2.5 | 95 | 82 | 95 | 91 | <100 | 6,600 | 34 | >180 |
| FRO | 6.4 | 6.0 | 80 | 80 | 99 | 93 | 580 | >13,000 | 37 | 56 |
| DAN | 2.3 | 2.8 | 98 | 93 | 120 | 110 | <100 | >13,000 | 32 | 72 |
| EER | 4.0 | 3.5 | 95 | 65 | 110 | 69 | 890 | >25,000 | 38 | >180 |
| DAM | 3.1 | 2.9 | 66 | 90 | 49 | 75 | 250 | 4,900 | 44 | 54 |
| TOR | 3.7 | 4.4 | 73 | 73 | 90 | 88 | 2,100 | >13,000 | 32 | 170 |
| CLA | 3.0 | 3.3 | 85 | 80 | 89 | 88 | 350 | >13,000 | 28 | 45 |
| MAN | 3.3 | 4.1 | 80 | 82 | 87 | 84 | 380 | 4,200 | 59 | 63 |
| MAT | 3.4 | 2.9 | 95 | 117 | 90 | 87 | 1,100 | 7,800 | 25 | 82 |
| Mean ± SEM | 3.5 ± 0.4 | 3.6 ± 0.4 | 85 ± 3.8 | 85 ± 4.9 | 92 ± 6.4 | 87 ± 8.3 | 650 ± 210 | 11,000 ± 2,100 | 37 ± 3.4 | 100 ± 19 |
| p* | 0.6 | | 0.9 | | 0.4 | | 0.004 | | 0.004 | |
| SakSTAR($K_{74}$) | | | | | | | | | | |
| UE | 4.6 | 3.9 | 110 | 76 | 100 | 61 | 3,300 | >13,000 | 27 | 40 |
| ENG | 3.0 | 2.9 | 130 | 130 | 100 | 120 | 610 | 4,700 | 27 | 29 |
| COX | 2.9 | 3.8 | 100 | 110 | 100 | 120 | <100 | 6,100 | 23 | 52 |
| MAN | 3.4 | 3.7 | 67 | 67 | 93 | 103 | <100 | 4,900 | 27 | 62 |
| VHE | 1.8 | 2.2 | 99 | 74 | 98 | 69 | 270 | >12.500 | 34 | 51 |
| MUL | 2.9 | 2.8 | 100 | 73 | 120 | 91 | 2,100 | 5,700 | 33 | 54 |
| BUR | 3.5 | 4.0 | 110 | 90 | 100 | 90 | 240 | 8,000 | 21 | 23 |
| NIJ | 2.5 | 2.5 | 95 | 92 | 97 | 94 | 400 | 11,000 | 21 | 23 |
| [POE**] | 2.3 | 2.4 | 98 | 89 | 100 | 100 | <100 | 4,800 | 31 | 68 |
| VBE | 3.6 | 4.5 | 130 | 110 | 120 | 100 | 460 | 4,200 | 22 | 117 |
| SME | 2.8 | 3.4 | | | | | 420 | 1,800 | 30 | 100 |
| WOL | 3.2 | 3.7 | 120 | 97 | 100 | 92 | 1,000 | 20,000 | 27 | 41 |
| Mean ± SEM | 3.1 ± 0.2 | 3.4 ± 0.2 | 110 ± 5.1 | 93 ± 6.0 | 100 ± 2.3 | 94 ± 5.1 | 820 ± 300 | 8,300 ± 1,600 | 27 ± 1.4 | 54 ± 9.1 |
| p* | 0.07 | | 0.007 | | 0.1 | | 0.001 | | 0.001 | |
| SakSTAR($K_{74}$ER) | | | | | | | | | | |
| JAC | 2.7 | 3.0 | 110 | 110 | 97 | 100 | <100 | 220 | 36 | >180 |

TABLE 8-continued

Coagulation parameters before and after administration of SakSTAR, SakSTAR($K_{74}$) or SakSTAR($K_{74}$ER) in patients with peripheral arterial occlusion.

| Compound | Fibrinogen (g/l) | | Plasminogen (%) | | $\alpha_2$-antiplasmin (%) | | D-dimer (ng/ml) | | aPTT (s) | |
|---|---|---|---|---|---|---|---|---|---|---|
| Patient Id. | Before | After | Before | After | Before | After | Before | Peak | Before | After |
| MAE | 3.5 | 4.2 | 110 | 110 | 95 | 99 | 250 | 1,400 | 28 | 28 |
| CRA | 3.4 | 3.8 | 89 | 91 | 97 | 95 | 430 | 1,300 | 35 | 89 |
| VDB | 6.2 | 6.6 | 100 | 100 | 85 | 90 | 970 | 3,700 | 32 | 42 |
| DUN | 4.2 | 3.9 | 100 | 90 | 93 | 86 | 200 | 10,000 | 31 | 45 |
| DEL | 3.2 | 2.7 | 91 | 76 | 96 | 88 | <100 | 4,700 | 37 | 61 |
| Mean ± SEM | 3.9 ± 0.5 | 4.0 ± 0.6 | 100 ± 3.5 | 96 ± 5.2 | 94 ± 1.9 | 94 ± 2.8 | 340 ± 140 | 3,500 ± 1,500 | 33 ± 1.4 | 74 ± 23 |
| p* | 0.8 | | 0.2 | | 1.0 | | 0.03 | | 0.06 | |

For calculations of mean ± SEM "<" and ">" were disregarded. * by paired Student's test or Mann-Withney test, as applicable. ** not included in calculations of mean ± SEM.

I claim:

1. Staphylokinase derivatives having the amino acid sequence as depicted in FIG. 1 (SEQ ID NO: 5) in which one or more amino acids in one or more underlined cluster have been replaced by another amino acid thus reducing the reactivity with a panel of murine monoclonal antibodies or with pooled plasma of patients treated with wild-type staphylokinase.

2. Staphylokinase derivatives as claimed in claim 1 having the amino acid sequence as depicted in FIG. 1 (SEQ ID NO: 5) in which one or more amino acids in one or more underlined cluster have been replaced by alanine thus destroying the corresponding epitope(s).

3. Staphylokinase derivative SakSTAR ($K_{74}$) having the amino acid sequence as depicted in FIG. 1 (SEQ ID NO: 5) in which the amino acid Lys on position 74, has been replaced by alanine thus altering the corresponding epitope.

4. Staphylokinase derivative SakSTAR (G36X, $K_{74}$X) having the amino acid sequence as depicted in FIG. 1 (SEQ ID NO: 5) in which the amino acids Gly in position 36 and Lys in position 74 have been replaced with another amino acid, thus altering the corresponding epitopes.

5. Method for producing the staphylokinase derivatives as claimed in claim 1, comprising the steps of:

a. preparing a DNA fragment comprising the coding sequence of staphylokinase;

b. performing in vitro site-directed mutagenesis on the DNA fragment to replace one or more codons for wild-type amino acids by a codon for another amino acid;

c. cloning the mutated DNA fragment in a suitable vector;

d. transforming or transfecting a suitable host cell with the vector; and e. culturing the host cell under conditions suitable for expressing the DNA fragment.

6. Method as claimed in claim 5, wherein the DNA fragment is a 453 bp EcoRI-HindIII fragment of the plasmid pMEX602sakB, the in vitro site-directed mutagenesis is performed and the mutated DNA fragment is expressed in *E. coli.*

7. Pharmaceutical composition comprising at least one of the staphylokinase derivatives as claimed in claim 1, together with a suitable excipient.

8. Pharmaceutical composition for treating arterial thrombosis, comprising a staphylokinase derivative prepared by the method as claimed in claim 5, wherein the DNA fragment is a 466 bp EcoRI-HindIII fragment of the plasmid pMEX602SAK, the in vitro site-directed mutagenesis is performed by an oligonucleotide-directed mutagenesis system using the plasmid pMa/c and the repair deficient *E. Coli* strain WK6MutS, and the mutated DNA fragment is cloned in *E. Coli* strain WK6.

9. Staphylokinase derivatives as claimed in claim 1 having the amino acid sequence as depicted in FIG. 1 (SEQ ID NO: 5) in which one or more amino acids have been replaced by alanine thus reducing the reactivity of the derivatives with a monoclonal antibody panel of antibodies 17G11, 26A2, 30A2, 2B12 and 3G10.

10. Staphylokinase derivatives as claimed in claim 1 having the amino acid sequence as depicted in FIG. 1 (SEQ ID NO: 5) in which one or more amino acids have been replaced by alanine thus reducing the reactivity of the derivatives with a monoclonal antibody panel of antibodies 7H11, 25E1, 40C8, 24C4 and 1A10.

11. Staphylokinase derivatives as claimed in claim 1 having the amino acid sequence as depicted in FIG. 1 (SEQ ID NO: 5) in which one or more amino acids have been replaced by alanine thus reducing the reactivity of the derivative with a monoclonal antibody panel of antibodies 17G11, 26A2, 30A2, 2B12, 3G10, 7H11, 25E1, 40C8, 24C4 and 1A10.

12. Method as claimed in claim 5 wherein codons for amino acids, Gly36 and Lys74 of the DNA fragment are replaced by codons for another amino acid.

* * * * *

UNITED STATES PATENT AND TRADEMARK OFFICE
CERTIFICATE OF CORRECTION

PATENT NO. : 5,951,980 
DATED : September 14, 1999
INVENTOR(S) : Désiré José Collen

It is certified that error appears in the above-identified patent and that said Letters Patent is hereby corrected as shown below:

Column 1 Line 36 "(SEQ ID NO: 3)" should read --(SEQ ID NO: 5)--.

Column 2 Line 3 "NH2" should read --$NH_2$--.

Column 5 Line 60 "primeness" should read --primerless--.

Column 6 Line 20 "($K_{35}E_{75}$)", first occurrence, should read --($K_{35}E_{75}R$)--.

Column 12 Line 65 "5xcm" should read --5 x 13 cm--.

Column 14 Line 54 "(issued Sep. 8, 1994)" should read --(issued Aug. 9, 1994)--.

Column 15 Line 29 "15." should read --15.-- (delete bold).

Columns 15-16, Table 1, line 2 of title "to be insolubilized" should read --to insolubilized--.

Columns 15-16, Table 1, under column heading "Substituted amino acid", ninth Compound, "K3SA" should read --K35A--.

Columns 15-16, Table 1, column 2, twelfth Compound, "K3SA" should read --K35A--.

Columns 15-16, Table 1, column 2, row 13, "K3SA" should read --K35A--.

Columns 17-18, Table 1-cont'd, under Epitope III table, column heading "Substituted amino acids", ninth Compound, "K3SA" should read --K35A--.

UNITED STATES PATENT AND TRADEMARK OFFICE

CERTIFICATE OF CORRECTION

PATENT NO. : 5,951,980

DATED : September 14, 1999

INVENTOR(S) : Désiré José Collen

It is certified that error appears in the above-identified patent and that said Letters Patent is hereby corrected as shown below:

Columns 17-18, Table 1-cont'd, under Epitope III table, column 2, twelfth Compound, "K3SA" should read --K35A--.

Columns 17-18, Table 1-cont'd, under Epitope III table, column 2, 13th Compound, "K3SA" should read --K35A--.

Column 17 Table 2, column 2, eleventh Compound, "E38A, E7SA" should read --E38A, E75A--.

Column 17 Table 2, footnote, line 1: "› 65.000" should read --≥ 65.000--.

Column 17, Table 2, footnote line 2: "percent ot" should read --percent of--.

Columns 19-20, Table 3, under heading "Epitope I", fourth subheading "sB12" should read --2B12--.

Columns 19-20, Table 3, under heading "Epitope III", blank spaces under five subheadings in row 6 should read --2.8 2.9 1.5 1.5 0.9--, respectively.

Columns 19-20, Table 3, under heading "Epitope III, subheading "24C4" row 26, "57" should read --5.7--.

Columns 19-20, Table 3, row 42, next-to-last column, "46" should read --4.6--.

Columns 19-20, Table 3, row 43 (next-to-last row), next-to- last column, "35" should read --3.5--.

UNITED STATES PATENT AND TRADEMARK OFFICE

CERTIFICATE OF CORRECTION

PATENT NO. : 5,951,980

DATED : September 14, 1999

INVENTOR(S) : Désiré José Collen

It is certified that error appears in the above-identified patent and that said Letters Patent is hereby corrected as shown below:

Columns 19-20, Table 3, under second column, row 33, "1133A" should read --I133A--.

Columns 19-20, Table 3, second column, next-to-last row, "L116A, 5117A" should read --L116A, S117A--.

Columns 19-20, Table 3, under "Epitope I" subheading "30A2" row 32 "48" should read --4.8--.

Columns 21-22, Table 3-continued, under "Epitope I", subheading "sB12" should read --2B12--.

Columns 21-22, Table 3-continued, under "Epitope II", subheading "18F12", first row, "1i" should read --11--.

Columns 21-22, Table 3-continued, under "Epitope I", subheading "30A2", row 2 "46" should read --4.6--.

Columns 21-22, Table 3-continued, third column, row 3, "08" should read --88--.

Columns 21-22, Table 3-continued, under "Epitope II", subheading "7F10", row 10 "3A" should read --3.4--.

Columns 21-22, Table 3-continued, column 2, row 15, "A725" should read --A72S--.

Columns 21-22, Table 3-continued, next-to-last column, first row, "36" should read --3.6--.

UNITED STATES PATENT AND TRADEMARK OFFICE
CERTIFICATE OF CORRECTION

PATENT NO. : 5,951,980

DATED : September 14, 1999

INVENTOR(S) : Désiré José Collen

It is certified that error appears in the above-identified patent and that said Letters Patent is hereby corrected as shown below:

Columns 23-24, Table 4, in the title, "Absorptino" should read --Absorption--.

Columns 23-24, Table 4, column 2 row 4 "FY6A" should read --F76A--.

Columns 23-24, Table 4, column 2 row 19 "Y735" should read --Y73S--.

Columns 23-24, Table 4, column 4 row 19 "66" should read --86--.

Columns 23-24, Table 4, column 3 row 23 "5.3" should read --53--.

Columns 23-24, Table 4, column 1 row 54 "SakSTAR.M105016" should read --SakSTAR.M105106--.

Columns 23-24, Table 4, column 1 row 55 "SakSTAR.M103014" should read --SakSTARM103104--.

Columns 25-26, Table 5, line 2 of title "eleicited" should read --elicited--.

Column 26, Table 5, under "Spec. Act.", second occurrence, last row, insert "65" and shift "48" "33" and "58" over one column to line up under "Pool" "Subpool B" and "Subpool C", respectively.

Columns 25-26, Table 6, next-to-last column heading, "occluison" should read --occlusion--.

Columns 25-26, Table 6, column 1, sixth compound "TCR" should read --TOR--.

UNITED STATES PATENT AND TRADEMARK OFFICE
CERTIFICATE OF CORRECTION

PATENT NO. : 5,951,980

DATED : September 14, 1999

INVENTOR(S) : Désiré José Collen

It is certified that error appears in the above-identified patent and that said Letters Patent is hereby corrected as shown below:

Columns 25-26, Table 6, column 1, second subheading "SaKSTAR" should read --SakSTAR--.

Column 25-26, Table 6, column 1, under second subheading, third compound "CDX" should read --COX--.

Column 27-28, Table 6-continued, next-to-last column heading "occluison" should read --occlusion--.

Columns 27-28, Table 6-continued, column 5, fourth compound "aortabilliac" should read --aortabiiliac--.

Columns 27-28, Table 7, fourth column heading "injfusion" should read --infusion--.

Columns 27-28, Table 7, first column, fourth compound "EER" should read --BER--.

UNITED STATES PATENT AND TRADEMARK OFFICE
CERTIFICATE OF CORRECTION

PATENT NO. : 5,951,980

DATED : September 14, 1999

INVENTOR(S) : Désiré José Collen

It is certified that error appears in the above-identified patent and that said Letters Patent is hereby corrected as shown below:

Columns 27-28, Table 7, first column, first compound under second subheading "UE" should read --LIE--.

Columns 29-30, Table 7-continued, fourth column heading "injfusion" should read --infusion--.

Columns 29-30, Table 8, first column, first compound under second subheading "UE" should read --LIE--.

Columns 29-30, Table 8, under column heading "Peak", row for Compound "VHE", "12.500" should read --12,500--.

UNITED STATES PATENT AND TRADEMARK OFFICE

CERTIFICATE OF CORRECTION

PATENT NO. : 5,951,980

DATED : September 14, 1999

INVENTOR(S) : Désiré José Collen

It is certified that error appears in the above-identified patent and that said Letters Patent is hereby corrected as shown below:

Column 33 Line 56, Claim 1, "cluster" should read --clusters--.

Column 33 Line 59 delete "staphylokinase" and insert --Staphylokinase--.

Column 33 Lines 59-60 before the period insert --, wherein said Staphylokinase derivatives retain the enzymatic activity of the wild-type Staphylokinase--.

Column 33 Line 64, Claim 2, "cluster" should read --clusters--.

Column 36 Line 21, Claim 12, after "acids" delete comma --,--.

Signed and Sealed this

Thirtieth Day of May, 2000

Attest:

Q. TODD DICKINSON

*Attesting Officer*

*Director of Patents and Trademarks*

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
(A) LENGTH: 20
(B) TYPE: NUCLEIC ACID
(C) STRANDEDNESS: SINGLE
(D) TOPOLOGY: UNKNOWN (xi) SEQUENCE DESCRIPTION: SEQ ID NO: 1:

CAGGAAACAG AATTCAGGAG 20

(2) INFORMATION FOR SEQ ID NO: 2:

(i) SEQUENCE CHARACTERISTICS:
(A) LENGTH: 28
(B) TYPE: NUCLEIC ACID
(C) STRANDEDNESS: SINGLE
(D) TOPOLOGY: UNKNOWN (xi) SEQUENCE DESCRIPTION: SEQ ID NO: 2:

CAAAACAGCC AAGCTTCATT CATTCAGC 28

(2) INFORMATION FOR SEQ ID NO: 3:

(i) SEQUENCE CHARACTERISTICS:
(A) LENGTH: 28
(B) TYPE: NUCLEIC ACID
(C) STRANDEDNESS: SINGLE
(D) TOPOLOGY: UNKNOWN (xi) SEQUENCE DESCRIPTION: SEQ ID NO: 3:

CAAAACAGCC GAGCTTCATT CATTCAGC 28

-continued (2) INFORMATION FOR SEQ ID NO: 4:

(i) SEQUENCE CHARACTERISTICS:
(A) LENGTH: 41
(B) TYPE: NUCLEIC ACID
(C) STRANDEDNESS: SINGLE
(D) TOPOLOGY: UNKNOWN (xi) SEQUENCE DESCRIPTION: SEQ ID NO: 4:

TTCAGCATGC TGCAGTTATT TCTTTTCTGC AACAACCTTG G 41

(2) INFORMATION FOR SEQ ID NO: 5:

(i) SEQUENCE CHARACTERISTICS:
(A) LENGTH: 136
(B) TYPE: AMINO ACID
(C) STRANDEDNESS: SINGLE
(D) TOPOLOGY: UNKNOWN (xi) SEQUENCE DESCRIPTION: SEQ ID NO: 5:

```
Ser Ser Ser Phe Asp Lys Gly Lys Tyr Lys Lys Gly Asp Asp Ala
1               5                   10                  15

Ser Tyr Phe Glu Pro Thr Gly Pro Tyr Leu Met Val Asn Val Thr
                20                  25                  30

Gly Val Asp Ser Lys Gly Asn Glu Leu Leu Ser Pro His Tyr Val
                35                  40                  45

Glu Phe Pro Ile Lys Pro Gly Thr Thr Leu Thr Lys Glu Lys Ile
                50                  55                  60

Glu Tyr Tyr Val Glu Trp Ala Leu Asp Ala Thr Ala Tyr Lys Glu
                65                  70                  75

Phe Arg Val Val Glu Leu Asp Pro Ser Ala Lys Ile Glu Val Thr
                80                  85                  90

Tyr Tyr Asp Lys Asn Lys Lys Lys Glu Glu Thr Lys Ser Phe Pro
                95                  100                 105

Ile Thr Glu Lys Gly Phe Val Val Pro Asp Leu Ser Glu His Ile
                110                 115                 120

Lys Asn Pro Gly Phe Asn Leu Ile Thr Lys Val Val Ile Glu Lys
                125                 130                 135

Lys
```